(12) United States Patent
Isaacman

(10) Patent No.: US 9,365,532 B1
(45) Date of Patent: Jun. 14, 2016

(54) SYNTHESIS, COMPOSITION AND USE OF NOVEL THERAPEUTIC AND COSMETIC SCHIFF BASE PRODUCTS FORMED BY REACTION OF A CARBONYL CONTAINING MOEITY WITH A TRANSIMINATION NUCLEOPHILIC CATALYST AND THE USE OF TRANSIMINATION NUCLEOPHILIC CATALYSTS TO INCREASE THE RATE AT WHICH CARBONYL CONTAINING THERAPEUTIC AND COSMETIC ACTIVES FORM SCHIFF BASE PRODUCTS WITH BIOLOGICAL AMINES

(75) Inventor: Steven Isaacman, New York, NY (US)

(73) Assignee: Nanometics, LLC., New York, NY (US)

( * ) Notice: Subject to any disclaimer, the term of this patent is extended or adjusted under 35 U.S.C. 154(b) by 813 days.

(21) Appl. No.: 13/396,221

(22) Filed: Feb. 14, 2012

Related U.S. Application Data

(60) Provisional application No. 61/442,432, filed on Feb. 14, 2011, provisional application No. 61/502,466, filed on Jun. 29, 2011.

(51) Int. Cl.
| | | |
|---|---|---|
| *C07D 307/52* | (2006.01) | |
| *C07D 333/22* | (2006.01) | |
| *C07D 207/335* | (2006.01) | |
| *C07C 251/20* | (2006.01) | |

(52) U.S. Cl.
CPC ............ *C07D 307/52* (2013.01); *C07C 251/20* (2013.01); *C07D 207/335* (2013.01); *C07D 333/22* (2013.01)

(58) Field of Classification Search
CPC ... C07C 251/20; C07D 307/52; C07D 333/22
See application file for complete search history.

(56) References Cited

U.S. PATENT DOCUMENTS 5,744,598 A * 4/1998 Skalkos et al. ............... 540/472

OTHER PUBLICATIONS

Dursun et al., Glasnik Hemicara i thecnologa Bisne i Hersegovine (1969) No. 17 pp. 39-41.*
Chemical Abstract Registry entries 904626-23-9, 904626-21-7, 342020-73-9, and 342020-72-8, entered into STN Aug. 25, 2006, Aug. 24, 2006, and Jun. 18, 2001, respectively.*
Sosnovskikh et al., "Structure of reaction products of 3-cyanochromones with ethylenediamine" Russion Chemical Bulletin, International Edition (2010) vol. 59 No. 11 pp. 2151-2154.*
Roy et al., "Dioxouranium(VI) complexes of N-(orthovanillidene)-anthranilic acid and N-(vanillidene)-anthranilic acid" Transition Metal Chemistry (1987) vol. 12 pp. 137-140.*
Chemical Abstracts entry for JP62-153212, (Katsuta et al.) originally published Jul. 8, 1987.*
Drugarin et al., "Synthesis of new hippuric acid derivatives, Part 2. Azomethines of hippuric acid esters" Pharmazie (1981) vol. 36 No. 4 pp. 302-303.*
Topich et al., "Monomeric Polymer-Anchored Molybdenum( V) Coordination Complexes" Inorganic Chemstry (1982) vol. 21 pp. 2079-2082.*
Salon et al., "Fluoroimines from the reaction of fluoroamino acids or fluoroketo acids with the aldehyde or amine form of vitamin B6: part III. Influence of fluorine on the formation and the reactivity of fluoroimines derived from beta-fluoroaspartates or beta-fluorooxaloacetate" Journal of Fluorine Chemistry (1985) vol. 27 No. 4 pp. 361-370.*
Wyler et al., "Urnwandlung eines Betacyans in ein Betaxanthin Synthese von Indicaxanthin aus Betanin" Helvetica Chimica Acta (1965) vol. 48 n0. 2 pp. 39-40.*
Johnson et al., "Reaction of Hydantoin with Acetals" Journal of Organic Chemistry (1962) vol. 27 pp. 2077-2080.*
Deng et al., "Microwave Synthesis of Schiff-Base Complexes and Organic Tin" Advanced Materials Research (2011) vol. 201-203, pp. 2550-2553.*
Barluenga et al., "Regioselective Synthesis of 4,6,7-Trisubstituted Benzofurans from Furfural Imines and Nonheteroatom Stabilized Alkynylcarbene Complexes" J. Am. Chem. Soc. (2009) vol. 131 pp. 14628-14629.*

* cited by examiner

*Primary Examiner* — Eric Olson
(74) *Attorney, Agent, or Firm* — Henry D. Coleman; R. Neil Sudol

(57) ABSTRACT

The present invention relates to the synthesis, composition and use of novel moieties formed by reacting a transimination nucleophilic catalyst, molecular or polymeric, with carbonyl-containing therapeutic or cosmetic moieties. The resultant Schiff base product is highly reactive towards transimination with a biological amine. The catalyst and carbonyl-containing moiety can be molecular or polymeric, and the resultant chemical and physical properties of the Schiff base products can be engineered by appropriate selection of said catalyst. The present invention also relates to the synthesis, composition and use of novel moieties that are used as actives in sunless tanning preparations. The present invention also relates to the use of transimination nucleophilic catalysts to increase the rate at which a carbonyl-containing moiety reacts with a biological amine. The present invention also relates to the use of transimination nucleophilic catalysts to increase the rate and efficacy of commercial sunless tanning preparations. Improvements on stability and efficacy of said preparations are disclosed. While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

16 Claims, 8 Drawing Sheets

FIGURE 6A and B

*In Vivo* clinical studies

TABLE 2

SYNTHESIS, COMPOSITION AND USE OF NOVEL THERAPEUTIC AND COSMETIC SCHIFF BASE PRODUCTS FORMED BY REACTION OF A CARBONYL CONTAINING MOEITY WITH A TRANSIMINATION NUCLEOPHILIC CATALYST AND THE USE OF TRANSIMINATION NUCLEOPHILIC CATALYSTS TO INCREASE THE RATE AT WHICH CARBONYL CONTAINING THERAPEUTIC AND COSMETIC ACTIVES FORM SCHIFF BASE PRODUCTS WITH BIOLOGICAL AMINES

RELATED APPLICATIONS

This application claims the benefit of priority of provisional application Ser. No. US61/442,432, filed Feb. 14, 2011, entitled "Synthesis, Composition and Use of Novel Therapeutic and Cosmetic Schiff Base Products Formed by Reaction of a Carbonyl Containing Moiety With a Transimination Nucleophilic Catalyst and the Use of Transimination Nucleophilic Catalysts to Increase the Rate at which Carbonyl Containing Therapeutic and Cosmetic Actives Form Schiff Base Products with Biological Amines, and provisional application Ser. No. US61/502,466, filed Jun. 29, 2011, entitled "Acceleration of In Vivo Schiff Base Formation, Compounds Related Thereto and Therapeutic Uses Thereof, each of which applications is incorporated by reference in its entirety.

FIELD OF THE INVENTION

The present invention relates to the synthesis, composition and methods for use of imines (Schiff bases) and iminium cations formed by reacting a transimination nucleophilic catalyst, with aldehyde or ketone containing molecules, and their use to treat disease or impart color change on the skin. The present invention also relates to the use of transimination nucleophilic catalysts, to increase the rate at which xenobiotic carbonyl containing molecules react with endobiotic biological amines. The present invention also relates to the use of imines, based on pyridoxamine, that form stable Schiff bases with aldehydes and are useful for treating sickle cell disease.

BACKGROUND

Endobiotic biological amines are reactive targets for an assortment of therapeutic and cosmetic moieties. In particular, moieties that contain a carbonyl group, and more particularly an aldehyde or ketone, can interact with said biological amines by forming an imine (Schiff base). Formation of said imine is kinetically slow under physiological conditions and thermodynamically unfavorable.

As one non-limiting example, aliphatic and aryl aldehydes are known to form Schiff base adducts with hemoglobin and impact allosteric oxy-deoxy protein confirmations. Said aldehydes can be used to treat hemoglobinopathies including, but not limited to, sickle cell disease. Sickle cell disease is a global health issue, resulting from an autosomal recessive red blood cell disorder that most commonly affects those of African, Mediterranean and Asian decent (1). Over 13 million people worldwide, including ~100,000 Americans, are afflicted with the disorder, with ~300,000 babies born each year with SCD (2). The disease is a caused by an inherited hemoglobinopathy that impairs oxygen binding and enables polymers to form in the red blood cells (RBC), triggering episodes of acute sickle crisis whereby the shapes of the RBC are distorted and become rigid and sickle-shaped (1). The genetic mutation is manifested physiologically as the altered morphologically sickled RBC occlude circulation, resulting in localized ischemia, infarction, hemolytic anemia, organ damage and other debilitating acute and chronic effects (1). While the frequency, severity and duration of vaso-occlusive crises can vary amongst individuals, the episodes are extremely painful, recurrent and lead to a high rate of hospitalization and use of acute medical care facilities, with annual costs to the global healthcare system (3). The pain crisis is the hallmark feature of the disease, interfering profoundly with functioning and has defied all attempts to intervene with drugs that target the sickling process (4). One promising approach to treat acute episodes involves the use of aryl aldehydes that interact stoichiometrically with the N-terminal amino group of $\alpha$-Val1 of HbS, increasing the oxygen affinity and inhibiting the sickling of homozygous sickle red blood cells by affecting allosteric oxy-deoxy conformational transitions (6). The resultant Schiff base adduct is thought to be stabilized by intramolecular interactions between structural aspects of oxy-Hb at the $\alpha\alpha$-end of the central cavity (6). Preclinical studies with various aldehydes have shown promise in vitro where the hypoxia-induced formation of sickle cells was largely inhibited by high concentrations of aldehyde (7). In addition, certain aldehydes have been shown to prolong the survival time of mice exposed to severe hypoxia and can exhibit favorable pharmacokinetic properties including oral bioavailability, rapid absorption into the blood stream, and high specificity for HbS (7). The clinical utility of these aldehydes requires high concentrations to compensate for the slow rate of Schiff base adduct (aldehyde/Hemoglobin) formation at hemoglobin and it would be advantageous to increase the rate of reaction, and thereby decrease the concentration of therapeutic needed for efficacy.

As another non-limiting example, aldehyde-containing molecules can be used as adjuvants to other interventions (e.g., vaccination) to combat a variety of pathogens, cancers and chronic infections. Non-limiting examples of said aldehydes include, but are not limited to, synthetic and natural saponin fractions QS-21 from *Quillaja saponaria*. It has recently been demonstrated unequivocally that the QS-21 isomeric constituents are responsible for the adjuvanticity of the saponin fractions, and that the aldehyde located on the triterpene is required for the adjuvant mechanism of action through Schiff base interaction with a cellular target. The saponin fraction of QS-21 has been demonstrated to be a potent immunological adjuvant when mixed with keyhole limpet hemocyanin conjugate vaccines, as well as with other classes of subunit antigen vaccines. QS-21 adjuvant is composed of two isomers that include the apiose and xylose forms in a ratio of 65:35, respectively. The chemical syntheses of these two isomers in pure form have recently been disclosed).

As another non-limiting example, synthetic immune response modifiers including, but not limited to, Tucaresol (4(2-formyl-3-hydroxy-phenoxymethyl) benzoic acid) and its derivatives, and Isotucaresol and its derivatives can form Schiff base adducts with T-cell surface amines and, in the presence of an antigen, provides co-stimulatory signals to CD4+ T-cells, enhancing Th-cell priming and CD8 cytotoxic T-cell priming; leading to favorable therapeutic activity profiles in vivo (2-7). Results from a Tucaresol Phase I/II pilot study in HIV-positive patients show an increase in CD4+ counts, increase in cytotoxic effector T lymphocytes (CD8+/28−/45RA/57+), increase in HIV-specific CD8+, increase in IFN-□□ and increase in perforin-producing cells, while leaving HIV viraemia unaffected (6). Unfortunately, Tucaresol-related serious adverse events were observed in two patients (2/21) after the first dose and in patients that were viraemic when commencing treatment (6). Unnecessarily large concentrations of Tucaresol must be administered to elicit an efficacious response, as the physiological environment in vivo (pH=7.4) provides an unfavorable setting for rapid Schiff base formation between the Tucaresol aldehyde and T-cell amine to occur. The slow rate of Schiff base formation at T-cell amines and rapid clearance of small molecules by the renal system results in the majority of Tucaresol being unreacted and wasted (2,3). It would be advantageous to accelerate the rate of Schiff base formation in order to mitigate the dose of Tucaresol required for efficacy, and decrease the likelihood of adverse effects.

Carbonyl containing moieties are also useful for cosmetic applications. As another non-limiting example, reducing sugars including, but not limited to, dihydroxyacetone (DHA) and erythrulose are useful to impart a "tanned appearance" on the skin, and widely used in sunless tanning applications. In these applications, the reducing sugar forms a Schiff base adduct with amines of the skin and undergoes subsequent Maillard type reactions to form brown colored compounds that are responsible for the tanned appearance that is associated with sunless tanners. Ketoses containing greater than 5 carbons, and aldoses containing greater than 4 carbons exist predominantly in the cyclic, unreactive form and react kinetically slow with proteins of the skin. As such, their utility in sunless tanning preparations is extremely limited.

The physiological environment in vivo can limit the practical utility of said carbonyl molecules as physiological conditions provide an unfavorable setting for rapid Schiff base formation between a carbonyl (ketone or aldehyde) and endobiotic biological amine to occur. As the kinetics of Schiff base formation at endobiotic amines is slow and small molecules are rapidly cleared by the renal system or washed away from the skin/hair/nails, the majority of said aldehyde or ketone can remain unreacted and wasted. It would be advantageous to accelerate the rate of Schiff base formation with endobiotic amines and herein we provide a method to do so.

SUMMARY OF THE INVENTION

In one aspect, the present invention provides for novel antisickling compounds, and their pharmacologically acceptable salts, that are based on transimination nucleophilic catalysts (herein termed "catalyst(s)"). The compounds are imines that are formed by reacting said catalyst with an aldehyde or ketone-containing molecule (herein termed "carbonyl molecule"). The resultant imines have a pKa that is only ~2 units below that of the free amine, and consequently are significantly protonated under physiological conditions. As such, the imine compounds are reactive electrophiles that react with hemoglobin at kinetically fast rates, and at low concentrations.

In another aspect, the present invention provides for a method to increase the rate of reaction between hemoglobin and a carbonyl molecule that binds hemoglobin to alter its allosteric activity. In this aspect, the catalyst is co-administered with the carbonyl molecule to increase the rate of reaction between said carbonyl molecule and hemoglobin. In a living system, as the rate of reaction between said carbonyl molecule and hemoglobin is increased, the effective concentration of the carbonyl molecule required to ligate a given amount of hemoglobin is decreased. In this aspect, the method may be used to decrease the concentration of carbonyl molecule required for efficacy and mitigate any toxic effects associated with the carbonyl molecule.

In another aspect, the present invention provides for novel antisickling compounds, and their pharmacologically acceptable salts, that are based on pyridoxamine and pyridoxamine phosphate. The compounds are imines that are formed by reacting pyridoxamine or pyridoxamine phosphate with an aldehyde or ketone-containing molecule (herein termed "carbonyl molecule"). The resultant imines are particularly stable to hydrolysis and highly reactive to transimination with an endobiotic biological amine. This enhanced reactivity is attributed to the physicochemical properties of the pyridinium pharmacophore (13-17) and the net positive charge on the imine, which results from intramolecular hydrogen bonding to the phenol that is present ortho to the imine.

In another aspect, the present invention provides for a method to increase the rate of reaction between hemoglobin and a carbonyl molecule that binds hemoglobin to alter its allosteric activity. In this aspect, the pyridoxamine or pyridoxamine phosphate is co-administered with the carbonyl molecule to increase the rate of reaction between said carbonyl molecule and hemoglobin. In a living system, as the rate of reaction between said carbonyl molecule and hemoglobin is increased, the effective concentration of the carbonyl molecule required to ligate a given amount of hemoglobin is decreased. In this aspect, the method may be used to decrease the concentration of carbonyl molecule required for efficacy and mitigate any toxic effects associated with the carbonyl molecule.

In another aspect, the present invention provides for novel immunomodulator compounds, and their pharmacologically acceptable salts, that are based on transimination nucleophilic catalysts (herein termed "catalyst"). The compounds are imines that are formed by reacting said catalyst with an aldehyde or ketone-containing molecule (herein termed "carbonyl molecule"). The resultant imines have a pKa that is only ~2 units below that of the free amine, and consequently is significantly protonated under physiological conditions. As such, the imine compounds are reactive electrophiles that react with their endobiotic biological target at kinetically fast rates, and at low concentrations.

In another aspect, the present invention provides for a method to increase the rate of reaction between an endobiotic biological amine and a carbonyl molecule that modulates immune response through Schiff base interactions with biological amines. In this aspect, the catalyst is co-administered with the carbonyl molecule to increase the rate of reaction between said carbonyl molecule and a biological amine of the immune system. In a living system, as the rate of reaction between said carbonyl molecule and said amine is increased, the effective concentration of the carbonyl molecule required to ligate a given amount of biological amine is decreased. In this aspect, the method may be used to decrease the concentration of carbonyl molecule required for efficacy and mitigate any toxic effects associated with the carbonyl molecule. Preferred carbonyl molecules of this aspect include Tucaresol (4(2-formyl-3-hydroxy-phenoxymethyl) benzoic acid), Isotucaresol and derivatives of Tucaresol and Isotucaresol.

In another aspect, the present invention provides for novel adjuvants, and their pharmacologically acceptable salts, that are based on transimination nucleophilic catalysts (herein termed "catalyst", a "radical" of said catalyst being that which forms an imine moiety with a corresponding carbonyl compound). The adjuvants are imines that are formed by reacting said catalyst with saponins or saponin derivatives. Preferred saponins include natural or synthetic versions of *Quillaja saponaria*, specifically fraction QS-21. The catalyst is reacted with the triterpene aldehyde to create an imine that is significantly protonated under physiological conditions. As such, the imine compounds are reactive electrophiles that react with their endobiotic biological target at kinetically fast rates, and at low concentrations In another aspect, the present invention provides for a method to increase the rate of reaction between an endobiotic biological amine and an aldehyde or ketone-containing adjuvant. In this aspect, the catalyst is co-administered with the adjuvant to increase the rate of reaction between said adjuvant and a biological amine of the immune system. In a living system, as the rate of reaction between said adjuvant and said amine is increased, the effective concentration of the adjuvant required to ligate a given amount of biological amine is decreased. In this aspect, the method may be used to decrease the concentration of adjuvant required for efficacy and mitigate any toxic effects associated with the adjuvant, or to increase the activity of said adjuvant at a given concentration. Preferred adjuvants of this aspect include saponins, saponin derivatives, and natural and synthetic derivatives of *Quillaja saponaria* fractions.

In another aspect, the present invention provides for a method to increase the rate of reaction between an endobiotic biological amine of the skin, hair or nails and a reducing sugar. In this aspect, the catalyst is co-administered with the reducing sugar to increase the rate of reaction between said sugar and a biological amine of the skin, hair or nails. This method is particularly useful to increase the rate of appearance of a faux tan in sunless tanning products.

Preferred catalysts include those that are safe for use in mammals or on mammalian skin, hair or nails and include, but are not limited to, aniline derivatives and more specifically p-aminobenzoic acid (PABA), $C_1$-$C_{12}$ esters of PABA, p-aminohipporic acid (PAHA), $C_1$-$C_{12}$ esters of PAHA, o-aminobenzoic acid (OABA), $C_1$-$C_{12}$ and esters of OABA, 2-amino phenols, 4-amino-3-hydroxybenzoic acid, $C_1$-$C_{12}$ esters of 4-amino-3-hydroxybenzoic. Other preferred classes of catalyst include pyridoxamine, pyridoxamine-5-phosphate, proline, peptides with N-terminal prolines, an optionally substituted imidazolidinone (optionally substituted with one or two $C_1$-$C_3$ alkyl groups), and other primary, secondary, and aromatic amines with unusually low pKa values (i.e. a $pK_a$ of less than 6.0, preferably less than about 5.5, less than about 5.0, less than about 4.5, less than about 4.0).

Preferred carbonyl molecules include, but are not limited to; aldehyde and ketone containing molecules that shift the allosteric equilibrium of hemoglobin to the high oxygen affinity state; small molecule immunomodulators that form Schiff base adducts with biological amines of the immune system including, but not limited to, Tucaresol, Isotucaresol and derivatives of Tucaresol and Isotucaresol; adjuvants that form Schiff base adducts with biological amines of the immune system including, but not limited to, saponin derivatives, natural and synthetic versions of QS-21, and synthetic versions of QS-21 that retain an aldehyde. Said carbonyl molecules additionally include, but are not limited to, 5-hydroxymethyl-2-furfuraldehyde (5HMF), 5-ethyl-2-furfuraldehyde (5EF), 5-methyl-2-furfuraldehyde (5MF), 2-furfuraldehyde (FUF), benzaldehyde, salicylaldehyde, 3-hydroxybenzaldehyde, 4-hydroxybenzaldehyde, o-anisaldehyde, m-anisaldehyde, p-anisaldehyde, 2-carboxybenzaldehyde, 4-carboxybenzaldehyde, 2-chlorobenzaldehyde, 4-cyanobenzaldehyde, 4-dimethylaminobenzaldehyde, Helicin, 2,3-dihydroxybenzaldehyde, 2,4-dihydroxybenzaldehyde, o-vanillin, 5-nitrosalicylaldehyde, 3,4-dihydroxybenzaldehyde, vanillin, isovanillin, veratraldehyde, trans-cinnamaldehyde, pyridoxal, pyridoxal phosphate, valeraldehyde, cyclohexanecarboxaldehyde, glyceraldehyde, glucose, fructose, 2-hydroxyacetophenone, Tucarasol, Isotucaresol, QS-21-Api, QS-21-Xyl, and others.

The authors have surprisingly found that the imines, formed by reacting said catalysts with said carbonyl molecules, can be isolated under controlled conditions in the laboratory and that these imine compounds are surprisingly stable to hydrolysis and exhibit unique chemical and therapeutic advantages.

DETAILED DESCRIPTION OF THE INVENTION

Figure 1:
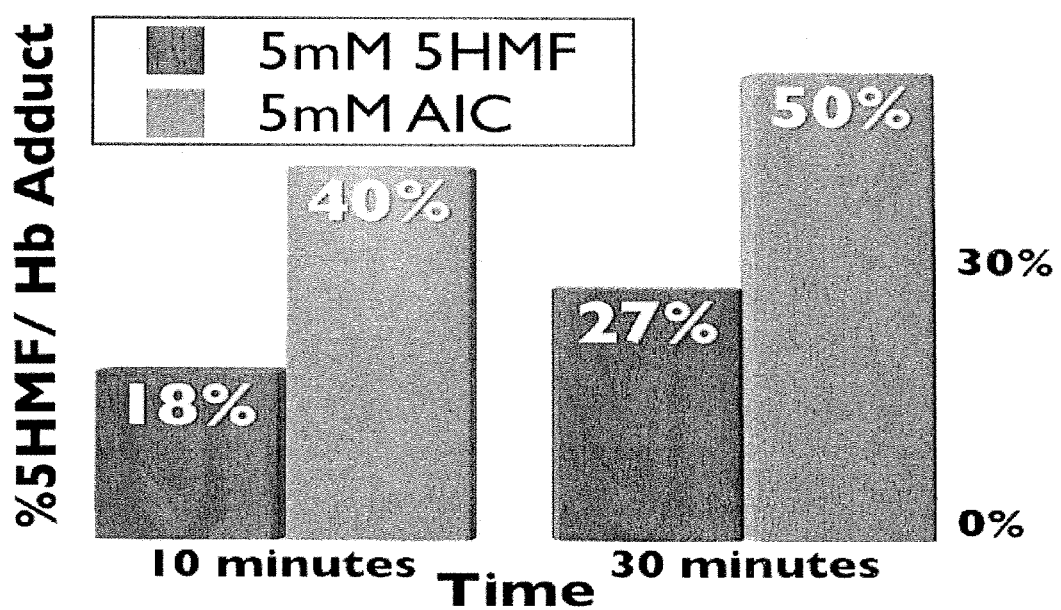
FIG. 1 shows ex vivo AIC experiments. Graph showing the percent 5HMF/HbS adduct formed in whole blood from a BERKγM mouse. 5 mM AIC or 5 mM 5HMF was used for these experiments. The AIC forms 5HMF/HbS Schiff base adducts at significantly enhanced rates.

The following terms shall be used to describe the present invention. In instances where a term is not provided with a specific definition herein, the common definition of a term given by those of ordinary skill within the context of the term's use is to be used to describe the invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

The term "compound" is used to describe any specific chemical compound disclosed herein. Within its use in context, the term generally refers to a single compound, but in certain instances may also refer to stereoisomers and/or optical isomers (including enantiopure compounds, enantiomerically enriched compounds and racemic mixtures) of disclosed compounds, as well as pharmaceutically acceptable salts, enantiomers, solvates and polymorphs thereof.

The term "target" is used to describe endobiotic biological amines of a living system. More specifically, it refers to biological amines of a mammalian system. These amines are nucleophilic sites of chemical attachment for a variety of aldehyde or ketone-containing moieties.

The term "co-administration" is used to describe the co-delivery of two or more molecules, in that both molecules are present in a mammal at the same time. The term "co-administration" is not limited to simultaneous delivery or delivery by the same route. For example, the catalyst and carbonyl molecule may be delivered by different methods (oral, intraperitoneal, intravenous, etc) at different times depending on the bioavailability and the pharmacokinetics of each molecule. In the present invention, the co-administration of a transimination nucleophilic catalyst and a carbonyl compound in a number of method/treatment aspects of the present invention may be utilized or even preferred, including for the treatment of cancer and/or HIV infections.

The term "carbonyl molecule" is used to describe an organic molecule that contains an aldehyde or ketone functional group.

The term "catalyst" is used to describe a transimination nucleophilic catalyst (also referred to in the literature as an iminium catalyst, or nucleophilic catalyst), either molecular or polymeric. More specifically, a molecule or polymer containing a primary or secondary amine that may condense with an aldehyde or ketone to form an imine that is significantly protonated under physiological conditions. The protonated imine is referred to as an "iminium cation" and is more susceptible to nucleophilic attack then the carbonyl molecule. A broad range of reactions including, but not limited to, transimination (trans-Schiffization) cycloadditions, nucleophilic additions, enamine formation and retroaldol reactions can be catalyzed using said catalyst. A of catalysts can be found in *Chem. Rev.*, 2007, 107 (12), 5416-5470.

The term "subject" is used to describe an animal, preferably a mammal (especially a human, pet, domesticated animal, etc.) capable of advantageously using compositions according to the present invention.

The term "pharmaceutically acceptable salt" of a compound, such as those contemplated in the current invention, is, for example, a salt of an acid, such as a carboxylate salt having as a counter ion, an inorganic cation such as sodium, potassium, magnesium, ammonium, etc., or the salt of a base, such as an ammonium salt having as counter ion an inorganic anion such as chloride, bromide, iodide, sulfate, sulfite, nitrate, nitrite, phosphate, and the like, or an organic anion such as a carboxylate, including acetate, malonate, pyruvate, propionate, fumarate, cinnamate, tosylate, and the like. In certain aspects of the invention, in order to promote the stability of the iminium compound, the compound formed as a zinc salt may be used to enhance stability of the iminium compound.

The term "personal care composition" or "personal care product" is used to describe a chemical composition used for the purpose of cleansing, conditioning, grooming, beautifying, or otherwise enhancing the appearance of the human body. Personal care products include skin care products, cosmetic products, antiperspirants, deodorants, perfume, toiletries, soaps, bath oils, feminine care products, hair-care products, oral hygiene products, depilatories, including shampoos, conditioners, hair straightening products and other haircare products, color cosmetics such as lipstick, creams, make-up, skin creams, lotions (preferably comprised of water-in-oil or oil-in-water emulsions), shave creams and gels, after-shave lotions and shave-conditioning compositions and sunscreen products, among numerous others. In preferred aspects, personal care compositions according to the present invention include make-up, lipstick, skin creams (to hide skin imperfections and/or to promote anti-wrinkling) and other skin-care products.

The term "effective" is used to describe an amount of a component or composition, which is used or is included in a formulation or composition within context, to produce an intended effect.

The term "isolated" refers to a compound which in a substantially pure state which has been separated from reaction products, solvents and/or other components which are used to synthesize or provide the product and/or solvents or other components. Isolated compounds according to the present invention which are isolatable and isolated are also stable, i.e. they may be in existence for more than a transitory period and often may be stored stably for periods of time, including long duration and further formulated into pharmaceutical compositions for administration or patients and subjects as otherwise described herein. It is noted that in using the term stable to describe compounds according to the present invention, zinc salts of the present invention as well as compounds which are stabilized using effective amounts of cyclodextrin (alpha cyclodextrin, beta cyclodextrin, hydroxypropyl-beta cyclodextrin, gamma cyclodextrin) and other sugars (e.g. trehalose, mannitol), among others.

The term "substantially pure" refers to the purity of a compound according to the present invention or a component which is used to provide a compound or composition according to the present invention, generally a purity of at least about 85%, at least about 90%, at least about 95%, at least about 96%, at least about 97%, at least about 98%, at least about 99%, at least about 99.5%, at least about 99.8%, at least about 99.9% or more.

The term "emulsion", "water-in-oil emulsion" or "oil-in-water emulsion", are used throughout the specification to describe certain personal care compositions according to the present invention. An "emulsion" according to the present invention is advantageously a cream or lotion (especially a skin cream or skin lotion) which is generally formed by the suspension of a very finely divided liquid, in this case water, in another liquid, in this case, an oil. In the present invention, an emulsion is formed when the water phase is compatabilized in the oil phase, such that the water phase becomes "hidden" within the oil phase. Alternatively, an emulsion also may be formed when the oil phase is compatabilized in the water phase, such that the oil phase is "hidden" within the water phase. The term emulsion is used to distinguish the present compositions from compositions which contain at least two visually distinct phases, i.e., an oil phase and a water phase. Emulsions can be used to provide a number of personal care formulations including skin creams, skin lotions, color cosmetics, conditioners, shampoo formulations, etc.

The term "oil" is used throughout the specification to describe any of various lubricious, hydrophobic and combustible substances obtained from animal, vegetable and mineral matter. Oils for use in the present invention may include petroleum-based oil derivatives such as purified petrolatum and mineral oil. Petroleum-derived oils include aliphatic or wax-based oils, aromatic or asphalt-based oils and mixed base oils and may include relatively polar and non-polar oils. "Non-polar" oils are generally oils such as petrolatum or mineral oil or its derivatives which are hydrocarbons and are more hydrophobic and lipophilic compared to synthetic oils, such as esters, which may be referred to as "polar" oils. It is understood that within the class of oils, that the use of the terms "non-polar" and "polar" are relative within this very hydrophobic and lipophilic class, and all of the oils tend to be much more hydrophobic and lipophilic than the water phase which is used in the present invention.

In addition to the above-described oils, certain essential oils derived from plants such as volatile liquids derived from flowers, stems and leaves and other parts of the plant which may include terpenoids and other natural products including triglycerides may also be considered oils for purposes of the present invention.

Petrolatum (mineral fat, petroleum jelly or mineral jelly) and mineral oil products for use in the present invention may be obtained from a variety of suppliers. These products may range widely in viscosity and other physical and chemical characteristics such as molecular weight and purity. Preferred petrolatum and mineral oil for use in the present invention are those which exhibit significant utility in cosmetic and pharmaceutical products and are "cosmetically compatible". Cosmetic grade oils are preferred oils for use in the present invention.

Additional oils for use in the present invention may include, for example, mono-, di- and tri-glycerides which may be natural or synthetic (derived from esterification of glycerol and at least one organic acid, saturated or unsaturated, such as for example, such as butyric, caproic, palmitic, stearic, oleic, linoleic or linolenic acids, among numerous others, preferably a fatty organic acid, comprising between 8 and 26 carbon atoms). Glyceride esters for use in the present invention include vegetable oils derived chiefly from seeds or nuts and include drying oils, for example, linseed, iticica and tung, among others; semi-drying oils, for example, soybean, sunflower, safflower and cottonseed oil; non-drying oils, for example castor and coconut oil; and other oils, such as those used in soap, for example palm oil. Hydrogenated vegetable oils also may be used in the present invention. Animal oils are also contemplated for use as glyceride esters and include, for example, fats such as tallow, lard and stearin and liquid fats, such as fish oils, fish-liver oils and other animal oils, including sperm oil, among numerous others. In addition, a number of other oils may be used, including $C_{12}$ to $C_{30}$ (or higher) fatty esters (other than the glyceride esters, which are described above) or any other acceptable cosmetic emollient.

In certain embodiments, oils for use in the present invention include petrolatum, mineral oil or mixtures of petrolatum and mineral oil where the amount of petrolatum to mineral oil (on a weight/weight basis) ranges from about 1:20 to about 10:1, about 1:5 to about 5:1, about 1:3 to about 1:1, depending upon the end use of the emulsion composition. The inclusion of petrolatum and/or mineral oil and/or the ratio of petrolatum to mineral oil in the present compositions will greatly influence the final viscosity of the emulsions and personal care compositions according to the present invention.

"R" substituents in the present invention may or may not be identical on the same molecule. Selection of "R" groups is dependent upon desired chemical and physical properties of said catalyst, and may change with application, as one of ordinary skill will readily recognize. Preferred "R" substituents other than hydrogen include, but are not limited to, $C_1$-$C_{30}$ (e.g., $C_1$-$C_{12}$, preferably $C_1$-$C_6$)alkyl, $C_1$-$C_{30}$ (e.g., $C_1$-$C_{12}$, preferably $C_1$-$C_6$)alkenyl, phenyl, $C_7$-$C_{30}$ (e.g., $C_7$-$C_{15}$, preferably $C_7$-$C_{12}$)aralkyl, $C_7$-$C_{30}$ (e.g., $C_7$-$C_{15}$, preferably $C_7$-$C_{12}$)aralkenyl, hydroxy, $C_1$-$C_{30}$ (e.g., $C_1$-$C_{12}$, preferably $C_1$-$C_6$)hydroxyalkyl, $C_1$-$C_{30}$ (e.g., $C_1$-$C_{12}$, preferably $C_1$-$C_6$)alkoxy, $C_1$-$C_{30}$ (e.g., $C_1$-$C_{12}$, preferably $C_1$-$C_6$) alkoxyalkyl, $C_7$-$C_{30}$ (e.g., $C_7$-$C_{15}$, preferably $C_7$-$C_{12}$) aralkoxy, $C_1$-$C_{30}$ (e.g., $C_2$-$C_{12}$, preferably $C_2$-$C_6$)acyloxy, halo, $C_1$-$C_{30}$ (e.g., $C_1$-$C_{12}$, preferably $C_1$-$C_6$)haloalkyl, nitro, amino, mono- and di-alkylamino wherein said alkyl is a $C_1$-$C_{30}$ (e.g., $C_1$-$C_{12}$, preferably $C_1$-$C_6$) alkyl, $C_1$-$C_{30}$) (e.g., $C_2$-$C_{12}$, preferably $C_2$-$C_6$)acylamino, carboxy, $C_2$-$C_{30}$ (e.g., $C_2$-$C_{12}$, preferably $C_2$-$C_6$)carboxyalkyl, $C_2$-$C_{30}$ (e.g., $C_2$-$C_{12}$, preferably $C_2$-$C_6$)carbalkoxy, $C_7$-$C_{30}$ (e.g., $C_7$-$C_{15}$, preferably $C_7$-$C_{12}$)carbaralkoxy, $C_3$-$C_{30}$ (e.g., $C_3$-$C_{12}$, preferably $C_3$-$C_6$)carbalkoxyalkyl, $C_3$-$C_{30}$ (e.g., $C_3$-$C_{12}$, preferably $C_3$-$C_6$)carbalkoxyalkenyl, $C_1$-$C_{30}$ (e.g., $C_1$-$C_{12}$, preferably $C_1$-$C_6$)aminoalkoxy, amido, mono- and di-alkylamido wherein said alkyl is a $C_1$-$C_{30}$ (e.g., $C_1$-$C_{12}$, preferably $C_1$-$C_6$) alkyl and $C_1$-$C_{30}$ (e.g., $C_1$-$C_{12}$, preferably $C_1$-$C_6$)N, N-cycloalkylamido, phenyl, or benzoyl. R substituents may contain functional groups such as carboxylic acids, poly (alkoxy) ethers, quaternary ammonium salts, and reactive functional groups.

"Alkyl" means a saturated $C_1$-$C_{30}$ (e.g., $C_1$-$C_{12}$, preferably $C_1$-$C_6$)aliphatic hydrocarbon, or a partially unsaturated aliphatic hydrocarbon, either branched-, straight-chained or cyclic. Preferred "loweralkyl" ($C_1$-$C_{12}$, preferably $C_1$-$C_6$) groups are branched, such as t-butyl and isopentyl. Preferred cyclic alkyl groups are $C_3$-$C_8$, or $C_5$-$C_6$ cyclic groups, or preferably cyclopentanate chains of $C_8$-$C_{35}$ long. "Alkoxy" refers to a $C_1$-$C_{30}$ (e.g., $C_1$-$C_{12}$, preferably $C_1$-$C_6$) alkyl-O-group. Preferred alkoxy groups are chosen from the list of fatty alcohols such as carpryl alcohol, 2-ethyl hexanol, dodecanol, myristyl alcohol, cetyl alcohol, palmitoleyl alcohol, isostearyl alcohol, stearyl alcohol, elaidyl alcohol, oleyl alcohol, linoleyl alcohol, elaidolinoleyl alcohol, linolenyl alcohol, elaidolinolenyl alcohol, riconoleyl alcohol, arachidyl alcohol, behenyl alcohol, erucyl alcohol, lignoceryl alcohol, sterol, ceryl alcohol, montanyl alcohol, myricyl alcohol, and geddyl alcohol. "Poly(alkoxy)" refers to linear alcohol ethers such as polyethylene glycol, having from 2 to 1000 or preferably 2 to 100 ethylene glycol (alkoxy) units. "Aryloxy" refers to a $C_6$-$C_{30}$ aryl-O-group. The preferred aryloxy groups are phenoxy and naphthoxy. "Aralkyl" means an alkyl group substituted by an aryl radical, preferably a $C_7$-$C_{20}$ aralkyl.

The term "personal care composition" or "personal care product" is used to describe a chemical composition used for the purpose of cleansing, conditioning, grooming, beautifying, or otherwise enhancing the appearance of the human body. Personal care products include skin care products, cosmetic products, antiperspirants, deodorants, perfume, toiletries, soaps, bath oils, feminine care products, hair-care products, oral hygiene products, depilatories, including shampoos, conditioners, hair straightening products and other hair care products, color cosmetics such as lipstick, creams, make-up, skin creams, lotions (preferably comprised of water-in-oil or oil-in-water emulsions), shave creams and gels, after-shave lotions and shave-conditioning compositions and sunscreen products, among numerous others. In preferred aspects, personal care compositions according to the present invention include make-up, lipstick, skin creams (to hide skin imperfections and/or to promote anti-wrinkling) and other skin-care products.

The term "effective" is used to describe an amount of a component or composition that is used or is included in a formulation or composition within context, to produce an intended effect.

The term "cancer" is used to describe the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Representative cancers include, for example, squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, glioblastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas, among others, which may be treated by the methods of treatment of the invention.

The term "traditional anti-cancer agent" is used to describe a compound other than those of the present invention which may be combined with a GTPase inhibitor as otherwise described herein for the treatment of cancer. Exemplary anti-cancer agents which may be used in the present invention include, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, $IPdR_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, gleevac, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258,); 3-[5-(methylsulfonylpiperadinemethyl)-indolylj-quinolone, vatalanib, AG-013736, AVE-0005, the acetate salt of [D-Ser(Bu t) 6,Azgly 10] (pyro-Glu-His-Trp-Ser-Tyr-D-Ser(But)-Leu-Arg-Pro-Azgly-$NH_2$ acetate [$C_{59}H_{84}N_{18}Oi_4$ —$(C_2H_4O_2)_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "human immunodeficiency virus" shall be used to describe human immunodeficiency virus I (HIV 1 and 2), the growth or replication of which may be inhibited or disease states of which may be treated using one or more methods according to the present invention. Viruses which may be treated according to the present invention include, for example, human immunodeficiency viruses 1 and 2 (HIV-1 and HIV-2), among others. The term HIV includes mutant strains of HIV including "drug resistant" or "multiple drug resistant" strains of the HIV virus which have mutated to be resistant to one or more clinically approved anti-HIV agents, including, in particular, HIV strains which are resistant to one or more NRTI compounds and/or NNRTI compounds. Exemplary HIV drug resistant strains which may be effectively treated using compounds according to the present invention include the following, among others: (defined by RT mutation)—XXBRU, K65R, Y115F, F116Y, Q151M, M184V, L74V, V75T, 4XZT, T215Y, K103N, T215Y/M184V, 5705-72, 488-101, C910-6, LA1M184V, G910-6 L100I, K101E, K103N, V106A, D110E, V179D, Y181C, D185E, D186E, Y188H, G190E, E138K, M41L, D67N, K70R, T215Y/F, K219Q/E, Y181C, K103N, L100I, Y188C/H among others.

The terms "ARC" and "AIDS" refer to syndromes of the immune system caused by the human immunodeficiency virus, which are characterized by susceptibility to certain diseases and T cell counts which are depressed compared to normal counts. HIV progresses from Category 1 (Asymptomatic HIV Disease) to Category 2 (ARC), to Category 3 (AIDS), with the severity of the disease.

A Category 1 HIV infection is characterized by the patient or subject being HIV positive, asymptomatic (no symptoms) and having never had fewer than 500 CD4 cells. If the patient has had any of the AIDS-defining diseases listed for categories 2 (ARC) or 3 (AIDS), then the patient is not in this category. If the patient's t-cell count has ever dropped below 500, that patient is considered either Category 2 (ARC) or Category 3 (AIDS).

A category 2 (ARC) infection is characterized by the following criteria: The patient's T-cells have dropped below 500 but never below 200, and that patient has never had any Category 3 diseases (as set forth below) but have had at least one of the following defining illnesses—

Bacillary angiomatosis
Candidiasis, oropharyngeal (thrush)
Candidiasis, vulvovaginal; persistent, frequent, or poorly responsive to therapy
Cervical dysplasia (moderate or severe)/cervical carcinoma in situ
Constitutional symptoms, such as fever (38.5 C) or diarrhea lasting longer than 1 month
Hairy leukoplakia, oral
Herpes zoster (shingles), involving at least two distinct episodes or more than one dermatome
Idiopathic thrombocytopenic purpura
Listeriosis
Pelvic inflammatory disease, particularly if complicated by tubo-ovarian abscess
Peripheral neuropathy According to the U.S. government, in Category 2 ARC, the immune system shows some signs of damage but it isn't life-threatening.

A Category 3 (AIDS) infection is characterized by the following criteria:

The patient's T-cells have dropped below 200 or
The patient has had at least one of the following defining illnesses—

Candidiasis of bronchi, trachea, or lungs
Candidiasis, esophageal
Cervical cancer, invasive**
Coccidioidomycosis, disseminated or extrapulmonary
Cryptococcosis, extrapulmonary
Cryptosporidiosis, chronic intestinal (greater than 1 month's duration)
Cytomegalovirus disease (other than liver, spleen, or nodes)
Cytomegalovirus retinitis (with loss of vision)
Encephalopathy, HIV-related
Herpes simplex: chronic ulcer(s) (greater than 1 month's duration); or bronchitis, pneumonitis, or esophagitis
Histoplasmosis, disseminated or extrapulmonary
Isosporiasis, chronic intestinal (greater than 1 month's duration)
Kaposi's sarcoma
Lymphoma, Burkitt's (or equivalent term)
Lymphoma, immunoblastic (or equivalent term)
Lymphoma, primary, of brain
*Mycobacterium avium* complex or *M. kansasii*, disseminated or extrapulmonary
*Mycobacterium tuberculosis*, any site (pulmonary** or extrapulmonary)
*Mycobacterium*, other species or unidentified species, disseminated or extrapulmonary
*Pneumocystis carinii* pneumonia
Pneumonia, recurrent**
Progressive multifocal leukoencephalopathy
*Salmonella* septicemia, recurrent
Toxoplasmosis of brain
Wasting syndrome due to HIV The term "traditional anti-HIV agent" refers to a compound which may be administered with one or more compounds according to the present invention, and includes anti-HIV agents such as nucleoside reverse transcriptase inhibitors (NRTI), non-nucleoside reverse transcriptase inhibitors, protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

The term "emulsion", "water-in-oil emulsion" or "oil-in-water emulsion", are used throughout the specification to describe certain personal care compositions according to the present invention. An "emulsion" according to the present invention is advantageously a cream or lotion (especially a skin cream or skin lotion) that is generally formed by the suspension of a very finely divided liquid, in this case water, in another liquid, in this case, an oil. In the present invention, an emulsion is formed when the water phase is compatibilized in the oil phase, such that the water phase becomes "hidden" within the oil phase. Alternatively, an emulsion also may be formed when the oil phase is compatabilized in the water phase, such that the oil phase is "hidden" within the water phase. The term emulsion is used to distinguish the present compositions from compositions that contain at least two visually distinct phases, i.e., an oil phase and a water phase. Emulsions can be used to provide a number of personal care formulations including skin creams, skin lotions, color cosmetics, conditioners, shampoo formulations, etc.

The term "oil" is used throughout the specification to describe any of various lubricious, hydrophobic and combustible substances obtained from animal, vegetable and mineral matter. Oils for use in the present invention may include petroleum-based oil derivatives such as purified petrolatum and mineral oil. Petroleum-derived oils include aliphatic or wax-based oils, aromatic or asphalt-based oils and mixed base oils and may include relatively polar and non-polar oils. "Non-polar" oils are generally oils such as petrolatum or mineral oil or its derivatives which are hydrocarbons and are more hydrophobic and lipophilic compared to synthetic oils, such as esters, which may be referred to as "polar" oils. It is understood that within the class of oils, that the use of the terms "non-polar" and "polar" are relative within this very hydrophobic and lipophilic class, and all of the oils tend to be much more hydrophobic and lipophilic than the water phase which is used in the present invention.

In addition to the above-described oils, certain essential oils derived from plants such as volatile liquids derived from flowers, stems and leaves and other parts of the plant which may include terpenoids and other natural products including triglycerides may also be considered oils for purposes of the present invention.

Petrolatum (mineral fat, petroleum jelly or mineral jelly) and mineral oil products for use in the present invention may be obtained from a variety of suppliers. These products may range widely in viscosity and other physical and chemical characteristics such as molecular weight and purity. Preferred petrolatum and mineral oil for use in the present invention are those which exhibit significant utility in cosmetic and pharmaceutical products and are "cosmetically compatible". Cosmetic grade oils are preferred oils for use in the present invention.

Additional oils for use in the present invention may include, for example, mono-, di- and tri-glycerides which may be natural or synthetic (derived from esterification of glycerol and at least one organic acid, saturated or unsaturated, such as for example, such as butyric, caproic, palmitic, stearic, oleic, linoleic or linolenic acids, among numerous others, preferably a fatty organic acid, comprising between 8 and 26 carbon atoms). Glyceride esters for use in the present invention include vegetable oils derived chiefly from seeds or nuts and include drying oils, for example, linseed, iticica and tung, among others; semi-drying oils, for example, soybean, sunflower, safflower and cottonseed oil; non-drying oils, for example castor and coconut oil; and other oils, such as those used in soap, for example palm oil. Hydrogenated vegetable oils also may be used in the present invention. Animal oils are also contemplated for use as glyceride esters and include, for example, fats such as tallow, lard and stearin and liquid fats, such as fish oils, fish-liver oils and other animal oils, including sperm oil, among numerous others. In addition, a number of other oils may be used, including $C_{12}$ to $C_{30}$ (or higher) fatty esters (other than the glyceride esters, which are described above) or any other acceptable cosmetic emollient.

In certain embodiments, oils for use in the present invention include petrolatum, mineral oil or mixtures of petrolatum and mineral oil where the amount of petrolatum to mineral oil (on a weight/weight basis) ranges from about 1:20 to about 10:1, about 1:5 to about 5:1, about 1:3 to about 1:1, depending upon the end use of the emulsion composition. The inclusion of petrolatum and/or mineral oil and/or the ratio of petrolatum to mineral oil in the present compositions will greatly influence the final viscosity of the emulsions and personal care compositions according to the present invention.

Aldehydes and ketones are poor electrophiles for Schiff base adduct formation under physiological conditions. The present invention provides for new chemical entities that are based on transimination nucleophilic catalysts. The new compounds contain imines with pKa values that result in a substantial amount of the imine being protonated under physiological conditions. As such, the protonated imine is a reactive electrophile that reacts with endobiotic biological amines at kinetically fast rates.

In one aspect, the present invention provides for the synthesis, composition and use of therapeutic imine compounds to treat disease. The compounds are highly reactive and effective therapeutics that react with their endobiotic biological targets at kinetically fast rates, and low concentrations. The compounds are formed by reacting a transimination nucleophilic catalyst with an aldehyde or ketone-containing molecule, and can be isolated under controlled conditions in the laboratory or formed in situ upon co-administration of said catalyst and said aldehyde or ketone molecule (herein carbonyl molecule). The resultant imine therapeutic compounds are significantly protonated under physiological conditions and subsequently highly reactive to transimination with the endobiotic target amine, thus providing highly reactive electrophiles with distinct chemical and therapeutic advantages.

In another aspect, the present invention also provides for a method to increase the rate of reaction between a carbonyl molecule and endobiotic biological amine. In this aspect, a transimination nucleophilic catalyst is co-administered with a carbonyl molecule in order to improve the rate of Schiff base formation between said carbonyl molecule and an endobiotic biological amine. When said carbonyl molecule is a therapeutic, the catalyst is useful to decrease the effective concentration of said carbonyl therapeutic and thereby useful to mitigate the likelihood of adverse, concentration dependent toxicity. While not wishing to be bound by theory, the authors believe that said catalyst and said therapeutic react in situ to form a more reactive imine or iminium cation, which subsequently undergoes transimination (trans-Schiffization) with the endobiotic amine target at kinetically fast rates.

In another aspect, the present invention provides for a method to treat sickle cell disease. Said catalyst is co-administered with a therapeutic aldehyde, and used to increase the rate of Schiff base adduct formation between the hemoglobin protein and said aldehyde. Use of said catalyst, or combination of catalysts, increases the rate of reaction between said aldehyde and hemoglobin. As a consequence of the increase in rate, the effective concentration of aldehyde required to ligate a given amount of protein is dramatically reduced.

In another aspect, the present invention provides for a method to modulate immune response. Said catalyst is co-administered with a therapeutic aldehyde, and used to increase the rate of Schiff base adduct formation between a T-cell and said aldehyde. Use of said catalyst, or combination of catalysts, increases the rate of reaction between said aldehyde and T-cell. As a consequence of the increase in rate, the effective concentration of aldehyde required to ligate a given amount of protein is dramatically reduced.

Preferred catalysts include those that are safe for use in mammals or on mammalian skin, hair or nails and include, but are not limited to, aniline derivatives and more specifically p-aminobenzoic acid (PABA), $C_1$-$C_{12}$ esters of PABA, p-aminohipporic acid (PAHA), $C_1$-$C_{12}$ esters of PAHA, o-aminobenzoic acid (OABA), $C_1$-$C_{12}$ and esters of OABA. Aniline and its derivatives meet the unique requirements for nucleophilic catalysis as the pKa of the resultant aniline Schiff base is only ~2 units below that of the free amine. Consequently, the resultant Schiff base (formed between said catalyst and said aldehyde or ketone-containing molecule) is significantly protonated under physiological conditions. The present invention utilizes nucleophilic catalysis with an aniline derivative, or other appropriate amine derivative, and is applicable to increase the rate of Schiff base formation between any aldehyde or ketone-containing molecule and an endobiotic amine. More specifically, the invention utilizes nucleophilic catalysis to mitigate the effective concentration of an aldehyde or ketone-containing therapeutic and decrease the likelihood of adverse effects. Other preferred classes of catalyst include pyridoxamine, pyridoxamine-5-phosphate, proline, proline derivatives, imidazolidinones, and other primary, secondary, and aromatic amines with unusually low pKa values. The authors have surprisingly found that the imines, formed by reacting said catalysts with said carbonyl molecule, can be isolated under controlled conditions in the laboratory. Said imines have unique properties, and are useful as therapeutics to treat a variety of disease states.

In another aspect, the invention provides for 5-membered heterocyclic imine compounds, and their pharmacologically acceptable salts, that covalently bind to and modify hemoglobin. Said imine compounds interact with amines of hemoglobin to affect the allosteric protein confirmation of said hemoglobin protein, and are useful to treat sickle cell disease. Thus, methods for using compounds to treat sickle cell disease in humans are described. Said imine compounds react with hemoglobin in a transaldimination reaction (with little or no activation energy, i.e. essentially an isoenergetic reaction) and accordingly requires very low levels of therapeutic. As such, the imine compounds have little or no toxicity, as the efficiency of in vivo protein modification is very high.

In another aspect, the invention provides for new molecules, designed through molecular modeling, that are engineered to demonstrate improved thermodynamic stability in the binding pocket of hemoglobin at the αα-end of the central cavity. Using data from the crystal structures of the Hb relaxed states bound to furfural or 5HMF, we generated images (Discovery Studio Visualizer) representing the binding site residues in the water filled cavity. The 5HMF aldimine adduct is less flexible and more stable in the binding cavity due to the more extensive hydrogen bonding network formed between the two 5HMF aldimine adducts, six water molecules and α1 and α2 chains. The furfural aldimine adduct is more flexible and less stable in the binding site as a result of the reduced hydrogen bonding contacts (2 furfural:4 H2O). These images suggest that reducing the flexibility and increasing the hydrogen bonding interactions with the cavity water molecules can stabilize the resultant aldimine adduct.

Sickle Cell Disease

Sickle cell disease (SCD) is a global health issue, resulting from an autosomal recessive red blood cell disorder that most commonly affects those of African, Mediterranean and Asian decent (1). Over 13 million people worldwide, including ~100,000 Americans, are afflicted with the disorder, with ~300,000 babies born each year with SCD (2). The disease is a caused by an inherited hemoglobinopathy that impairs oxygen binding and enables polymers to form in the red blood cells (RBC), triggering episodes of acute sickle crisis whereby the shapes of the RBC are distorted and become rigid and sickle-shaped (1). The genetic mutation is manifested physiologically as the altered morphologically sickled RBC occlude circulation, resulting in localized ischemia, infarction, hemolytic anemia, organ damage and other debilitating acute and chronic effects (1). While the frequency, severity and duration of vaso-occlusive crises can vary amongst individuals, the episodes are extremely painful, recurrent and lead to a high rate of hospitalization and use of acute medical care facilities, with annual costs to the US healthcare system of up to ~$1B (3). The pain crisis is the hallmark feature of the disease, interfering profoundly with functioning and has defied all attempts to intervene with drugs that target the sickling process (4).

While repeated transfusions of red blood cells can greatly reduce the severity of disease, and hematopoietic stem cell transplants can cure SCD, the only approved disease-modifying therapy for SCD remains hydroxyurea (HU). HU is efficacious as a prophylactic to reduce the frequency of crises, but the proper use requires months of strict compliance, self-administration by the patient, and careful monitoring by the physician to ensure proper dosing schedules before an effect from the therapy can be realized (2). For these reasons, HU has not been widely adopted as a prophylactic (2). HU is not suitable as a therapeutic to treat imminent events of crisis or stop the progression of crisis once it has begun. In fact, to date there is with 5HMF. The formation no commercial therapeutic to avert imminent episodes of crisis or attenuate acute events of crisis once they have begun, as the clinical utility of these drugs has been limited by the toxicity associated with the high concentration of therapeutic needed to inhibit sickling (5). New anti-sickling agents that react with hemoglobin (Hb) at low concentrations are urgently needed to avert or treat episodes of sickle crisis.

One promising approach to treat acute episodes involves the use of the aryl aldehydes including, but not limited to, 5-Hydroxymethyl-2-furfural (5HMF). 5HMF interacts stoichiometrically with the N-terminal amino group of α-Val1 of HbS (2 5HMF:1 HbS), increasing the oxygen affinity and inhibiting the sickling of homozygous sickle red blood cells by affecting allosteric oxy-deoxy conformational transitions (6). The resultant 5HMF/HbS Schiff base adduct is thought to be stabilized by intramolecular interactions between the 5'-hydroxymethyl group and structural aspects of oxy-Hb at the ☐☐-end of the central cavity; as inferred from differences in efficacy between furfural, 5-methyl-2-furfural (5MF) and 5HMF (6). Preclinical studies with 5HMF have shown promise in vitro where the hypoxia-induced formation of sickle cells was largely inhibited by high concentrations of 5HMF (7). In addition, 5HMF prolonged the survival time of mice exposed to severe hypoxia and has been shown to exhibit favorable pharmacokinetic properties including oral bioavailability, rapid absorption into the blood stream, and high specificity for HbS (7).

In one aspect of the present invention, the transimination nucleophilic catalyst PABA is reacted with 5-hydroxymethyl-2-furfural to create a new imine compound. Said imine compound, or its pharmacologically acceptable salts, can be isolated under controlled conditions in the laboratory and reacts with Hemoglobin at a much faster rate in a trans-Schiff base reaction (transimination), when compared to 5HMF alone (aldimine reaction). During our studies the imine compound, formed by reacting PABA with 5HMF, was isolated and chemically characterized as a new chemical entity. Said imine compound is a more reactive electrophile as compared to 5HMF and reacts with HbS at faster rates than free 5HMF under physiological conditions. Furthermore, said imine is more stable in terms of its degradation in the presence of air, light and moisture; an intrinsic limitation of 5HMF as a therapeutic agent. This represents an important observation when considering drug stability requirements (10). The approach of the present invention is focused on the in vivo site selective reversible chemical modification of Val-1(α) HbS, as the Schiff base adducts formed at this amino group remains the only known modification that is stabilized by the non-covalent interactions, and Schiff base adducts at other sites on HbS (and other proteins) are expected to dissociate rapidly as the 5HMF concentration decreases due to removal by the circulatory system.

The use of aniline as a nucleophilic catalyst to create iminium cation intermediary species was exemplified by Dawson et al, who showed that buffers containing aniline, and p-methoxyaniline dramatically improve the rates of chemoselective bio-conjugation reactions between xenobiotic aldehydes and amine nucleophiles in solution. (11-14) The toxicity of aniline precludes its use as a therapeutic modality in vivo, but the many derivatives of aniline have been shown to exhibit excellent toxicological profiles in humans. (15-17) p-Aminobenzoic acid (PABA) is widely used as a topical sunscreen and ingestible ingredient in nutritional supplements (18). PABA is extremely well tolerated in humans, and has no reported side effects at daily doses below 12 grams (19). The pharmacokinetic profile of PABA in humans is well known, and the major metabolite, p-aminohippuric acid (PAHA), can also catalyze 5HMF/HbS adduct formation. As such, PABA is a preferred catalyst of the present invention.

Transimination nucleophilic catalysts (aniline and p-methoxyaniline) are known to enhance the rates of biomolecular ligations between □-effect amines (hydrazines and aminooxy groups) and aldehydes in aqueous solutions. (11-14) Jencks' requirement (20) for such catalysis is 1) fast formation of a thermodynamically unstable Schiff base (i.e., with aniline) that is more readily protonated for the transimination reaction than the starting aldehyde and 2) subsequent transimination to form a thermodynamically stabilized product. This strategy is useful in chemical biology to increase the rate, and overall yield, of biomolecular labeling reactions and conjugations (11). However, to date, the utility of this strategy has been restricted to biomolecules containing hydrazine or aminoxy derivatives that form thermodynamically stable hydrazone and oxime products in aqueous solutions due to the favorable electronic effect of extended conjugation (14). The use of catalysts to increase the rate of Schiff base adduct formation between a primary amine (like that of α-Val1 of HbS) and an aldehyde has not been reported because the resultant Schiff base product is expected to be as unstable in aqueous solution as the aniline Schiff base intermediate and therefore cannot benefit from aniline catalysis (20). The situation with adducts formed between aldehydes, like 5HMF, and HbS is unique as the Schiff base product is stabilized by non-covalent interactions at the □□-end of the central cavity of HbS, thus covalently bound (reversible) 5HMF provides its own thermodynamic stabilization with rates of formation that can be impacted by the presence of catalyst. Our research team recognizes the utility of PABA as an in vivo organocatalyst to treat a variety of disease states whereby the efficacy of the therapeutic is dependent upon the rate or degree of Schiff base adduct formation.

The invention provides compounds of the formula

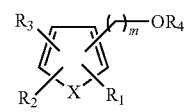

where $R_1$ is an imine C=N—V, its tautomer, or a pharmacologically acceptable salt C=$^+$NH—V, in that V is a transimination nucleophilic catalyst and more preferably a substituted aniline derivative and more specifically p-aminobenzoic acid (PABA) or a $C_1$-$C_{12}$ ester of p-aminobenzoic acid; $R_2$ and $R_3$ are the same or different and are H, OH, $C_1$-$C_{12}$ alkyl, $C_1$-$C_{12}$ alkoxy, $C_1$-$C_{12}$ hydroxyl-alkyl, halogen, aryl, or O-aryl; $R_4$ is H or a $C_1$-$C_{12}$ alkyl ester moiety; m=1-6; X=NH, O, S Se or P.

Exemplary embodiments of the compound are as follows:

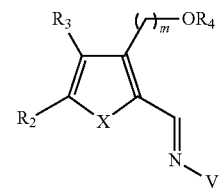

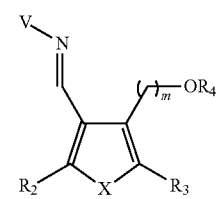

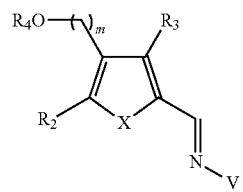

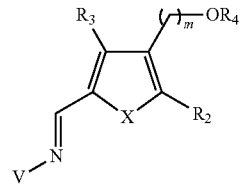

-continued

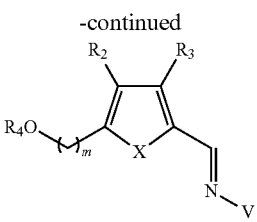

In a preferred embodiment of the invention, $R_1$ is an aniline derivative and more specifically p-aminobenzoic acid (PABA), o-aminobenzoic acid (OABA) or m-aminobenzoic acid (MABA) or a $C_1$-$C_{12}$ alkyl derivative of PABA, OABA or MABA whereby $R_6$ represents an H or a $C_1$-$C_{12}$ alkyl group, and the compound is of the formula

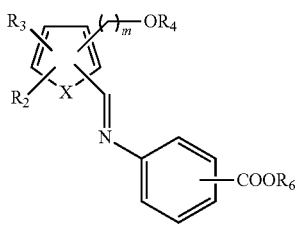

Examples of which include

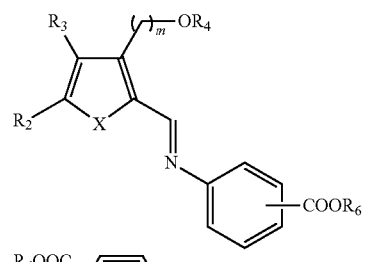

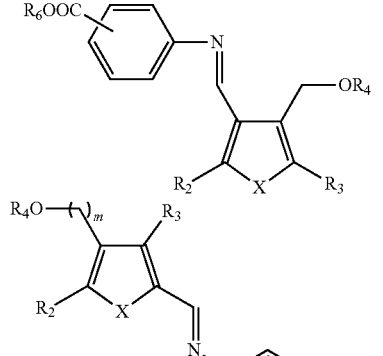

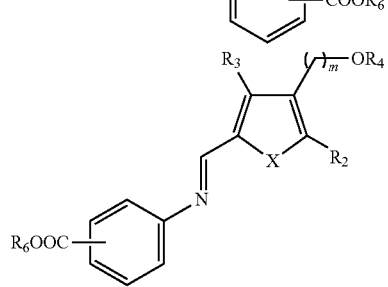

-continued

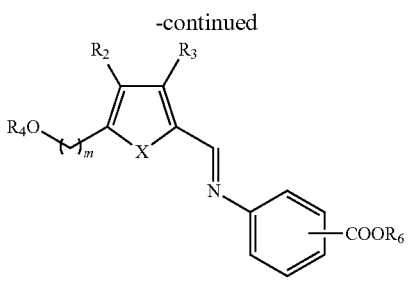

The invention additionally provides compounds of the formula

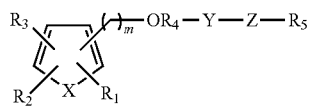

where $R_1$ is an imine C=N—V, its tautomer, or a pharmacologically acceptable salt C=$^+$NH—V, in that V is a transimination nucleophilic catalyst and more preferably a substituted aniline derivative and more specifically p-aminobenzoic acid (PABA), OABA, MABA or a $C_1$-$C_{12}$ ester of PABA, OABA or MABA; $R_2$ and $R_3$ are the same or different and are H, OH, $C_1$-$C_{12}$ alkyl, $C_1$-$C_{12}$ alkoxy, $C_1$-$C_{12}$ hydroxyl-alkyl, halogen, aryl, or O-aryl; $R_4$ and $R_5$ are the same or different and are a substituted or unsubstituted aromatic or heteroaromatic moiety, a substituted or unsubstituted alkyl or alkylnoic acid or ester moiety; m=1-6; X=NH, O, S Se or P; and wherein Y=a chemical linker which includes one to four chemical moieties selected from the group consisting of $CH_2$, CO, O, S, NH, NHCO and NHCONH; Z=$(CH)_n$ where n=1-4; and positions of Y and Z are interchangeable. Exemplary embodiments of the compound are as follows:

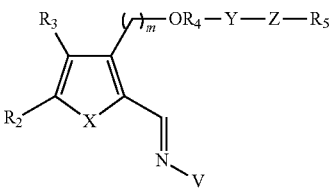

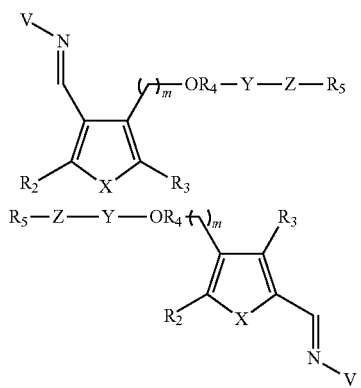

-continued

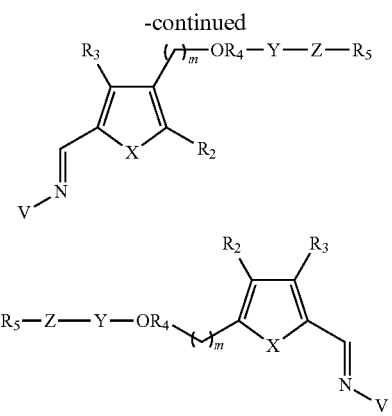

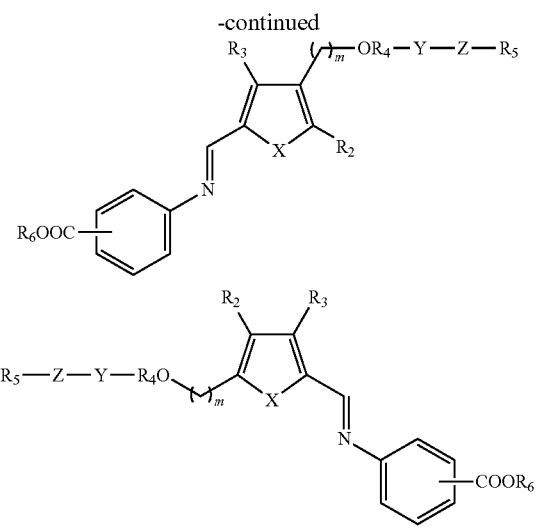

In a preferred embodiment of the invention, $R_1$ is an aniline derivative and more specifically p-aminobenzoic acid (PABA), o-aminobenzoic acid (OABA) or m-aminobenzoic acid (MABA) or a $C_1$-$C_{12}$ alkyl derivative of PABA, OABA or MABA whereby $R_6$ represents an H or $C_1$-$C_{12}$ alkyl group, and the compound is of the formula

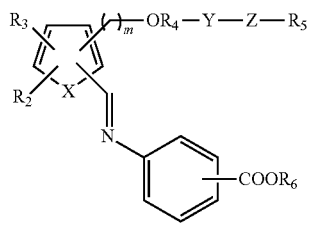

Examples of which include

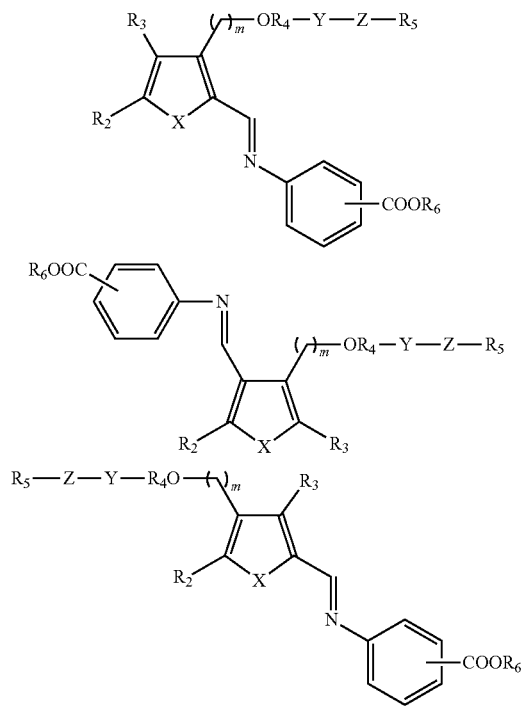

The invention additionally provides compounds of the formula

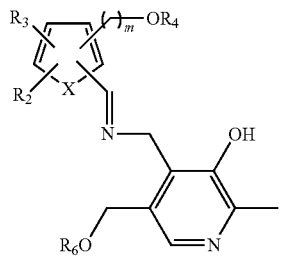

where $R_2$ and $R_3$ are the same or different and are H, OH, $C_1$-$C_{12}$ alkyl, $C_1$-$C_{12}$ alkoxy, $C_1$-$C_{12}$ hydroxyl-alkyl, halogen, aryl, or O-aryl; $R_4$ is a substituted or unsubstituted alkyl or alkylnoic acid or ester moiety; m=1-6; X=NH, O, S Se or P; m=1-6; X=NH, O, S Se or P; $R_6$ is H or phosphate. Exemplary embodiments of the compound are as follows:

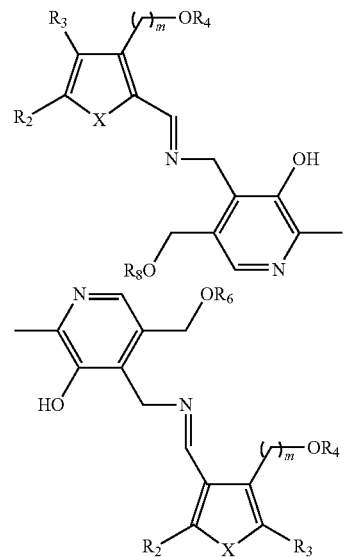

-continued

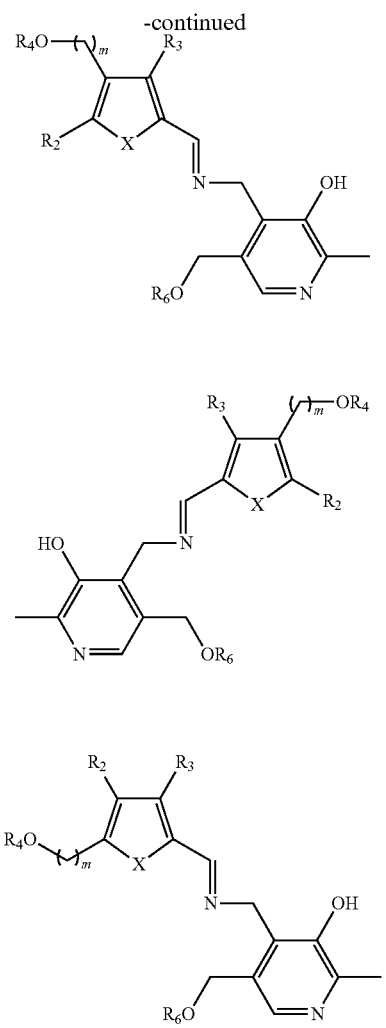

The invention additionally provides compounds of the formula

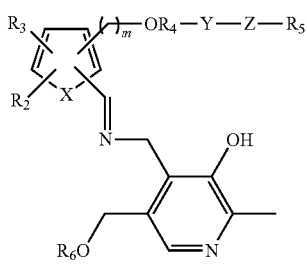

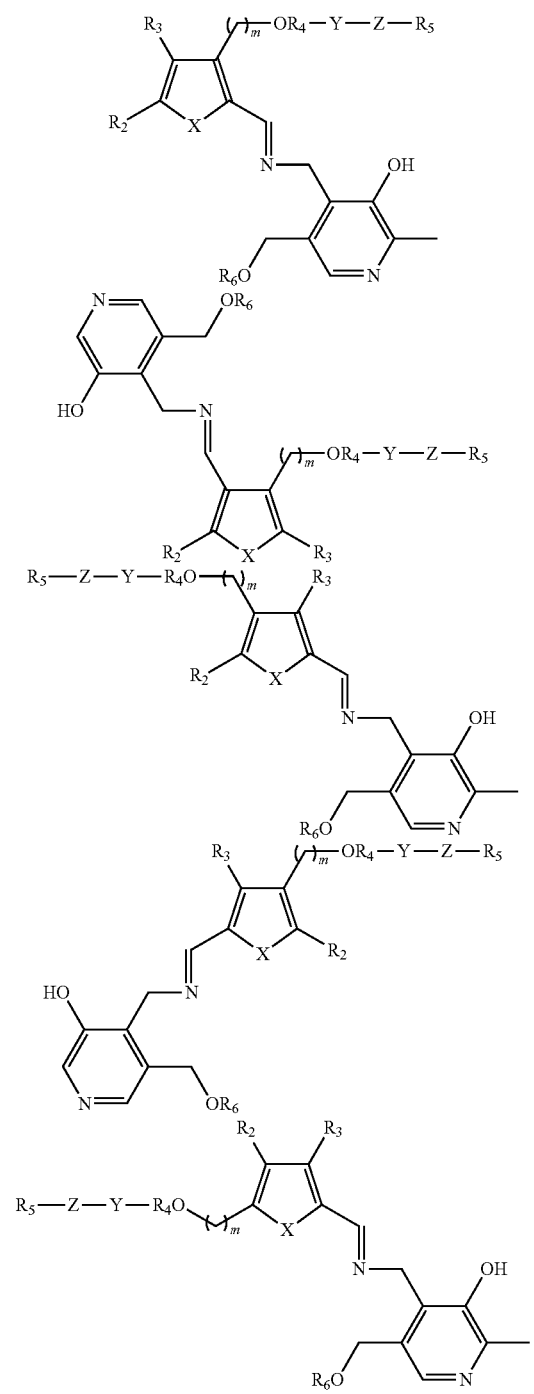

where $R_2$ and $R_3$ are the same or different and are H, OH, $C_1$-$C_{12}$ alkyl, $C_1$-$C_{12}$ alkoxy, $C_1$-$C_{12}$ hydroxyl-alkyl, halogen, aryl, or O-aryl; $R_4$ and $R_5$ are the same or different and are a substituted or unsubstituted aromatic or heteroaromatic moiety, a substituted or unsubstituted alkyl or alkylnoic acid or ester moiety; m=1-6; X=NH, O, S Se or P; and wherein Y=a chemical linker which includes one to four chemical moieties selected from the group consisting of $CH_2$, CO, O, S, NH, NHCO and NHCONH; Z=$(CH)_n$ where n=1-4; and positions of Y and Z are interchangeable and whereby R6 is an H or phosphate. Exemplary embodiments of the compound are as follows:

Small Molecule Immunomodulators for HIV and Other Chronic Diseases

HIV is an example of a global health issue, affecting over 1 million people in the United States and ~33 million people worldwide (1). While current antiretroviral therapies have greatly improved clinical prognoses, new strategies are needed to restore and enhance normal cell-mediated immunity. Immune response modifiers that are effective at low clinical doses, can assist in restoring the defects in cell-mediated immunity without increasing the viral load and that are specific for HIV immunity are needed as supplements to antiretroviral therapy (1).

One promising approach to restore immune response involves the use of the small molecule immune response modifiers with aryl aldehydes. Non-limiting examples of which include (IRM) Tucaresol (4(2-formyl-3-hydroxy-phenoxymethyl) benzoic acid) and Isotucaresol. In the presence of an antigen, Schiff base formation between the Tucaresol aldehyde and T-cell surface amines provides co-stimulatory signals to CD4+ T-cells, enhancing Th-cell priming and CD8 cytotoxic T-cell priming; leading to favorable therapeutic activity profiles in vivo (FIG. 2) (2-7). Results from a Tucaresol Phase I/II pilot study in HIV-positive patients show an increase in CD4+ counts, increase in cytotoxic effector T lymphocytes (CD8+/28−/45RA/57+), increase in HIV-specific CD8+, increase in IFN-! and increase in perforin-producing cells, while leaving HIV viraemia unaffected (6). Unfortunately, Tucaresol-related serious adverse events were observed in two patients (2/21) after the first dose and in patients that were viraemic when commencing treatment (6). Unnecessarily large concentrations of Tucaresol must be administered to elicit an efficacious response, as the physiological environment in vivo (pH=7.4) provides an unfavorable setting for rapid Schiff base formation between the Tucaresol aldehyde and T-cell amine to occur. The slow rate of Schiff base formation at T-cell amines and rapid clearance of small molecules by the renal system results in the majority of Tucaresol being unreacted and wasted (2,3)

In one aspect of the present invention, a transimination nucleophilic catalyst is used to increase the rate of reaction between Tucaresol and T-cell amines. The catalyst and Tucaresol react to form an intermediate species (AIC-4423) that subsequently reacts with T-cells at an accelerated rate in a trans-Schiff base reaction (FIG. 1). Upon reaction with T-cells, the Tucaresol/T-cell adduct is formed, and the benign catalyst is regenerated (FIG. 1). The increased rate of reaction of AIC-4423 with T-cells decreases the molar ratio of Tucaresol needed to achieve a desired level of in vivo Tucaresol/T-cell adduct and stimulate Th1 type immune response, thereby leading to effective immune potentiation at lower concentrations.

In another aspect, the invention provides for aromatic imine compounds, and their pharmacologically acceptable salts, which are useful as adjuvants to modulate immune response in mammals. Said imine compounds react with endobiotic biological amines in a transaldimination reaction (with little or no activation energy, i.e. essentially an isoenergetic reaction) and accordingly requires very low levels of therapeutic. As such, the imine compounds have mitigated toxicity as the efficiency of in vivo protein modification is very high.

The invention provides compounds of the formula

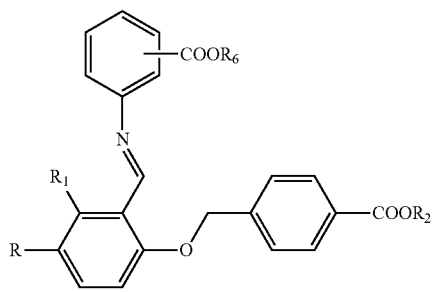

wherein R and R1 are each independently hydrogen or —C(O)H, an optionally substituted $C_{1-20}$ alkyl group, a saccharyl group or a group represented by the formula —C(O)—[C(R_3)(R_4)]n-COOH or —[C(R_3)(R_4)]n-COOH;

$R_3$ and $R_4$ is independently selected from hydrogen or an optionally substituted $C_{1-10}$ alkyl group or an unsubstituted $C_{1-10}$ alkyl group;

n is an integer from 1 to 5;

$R_2$ is selected from hydrogen, a substituted $C_{1-20}$ alkyl group, an unsubstituted $C_{1-20}$ alkyl group and a group represented by the formula —$(CH_2)_m CH(OH)(CH_2)OR_5$, wherein m and p are each independently 1 or 2, and $R_5$ is a $C_{1-20}$ acyl group, or a group represented by the formula

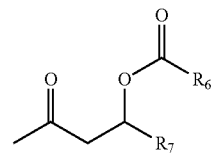

wherein j is an integer from 1 to 5, and $R_6$ and $R_7$ are each independently selected from the group of a hydrogen, an optionally substituted $C_{1-20}$ alkyl group or a pharmacologically acceptable salt thereof. Examples of the above compounds include

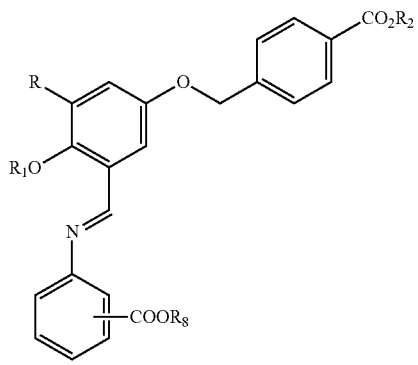

Wherein each of R, $R_1$ and $R_2$ are as described above and $R_8$ is H or an optionally substituted $C_1$-$C_{12}$ alkyl group.

In yet another aspect, the present invention provides for the synthesis, composition and use of the Activated Iminium Cation formed by the reaction of IsoTucaresol or its derivatives, and a transimination nucleophilic catalyst, and its use as an immune response modifier. Preferred catalysts include, but are not limited to, p-aminobenzoic (PABA) acid, p-aminohippuric acid (PAHA), anthranilic acid and derivatives of p-aminobenzoic (PABA) acid, p-aminohippuric acid (PAHA) and anthranilic acid.

The invention provides compounds of the formula

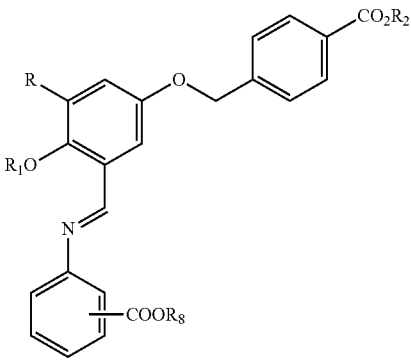

where R represents hydrogen or —C(O)H, an optionally substituted $C_{1-20}$ alkyl group, a saccharyl group or a group represented by the formula —C(O)—[C(R$_3$)(R$_4$)]n-COOH or —[C(R$_3$)(R$_4$)]n-COOH, wherein each R$_3$ and R$_4$ independently is a member selected from hydrogen, a substituted $C_{1-10}$ alkyl group, an unsubstituted $C_{1-10}$ alkyl group. The symbol n represents an integer from 1 to 5. The symbol R$_2$ represents a member selected from hydrogen, an optionally substituted $C_{1-20}$ alkyl group or a group represented by the formula —(CH$_2$)$_m$CH(OH)(CH$_2$)OR$_5$, wherein m and p are independently 1 or 2, and R$_5$ is a $C_{1-20}$ acyl group, or a group represented by the formula

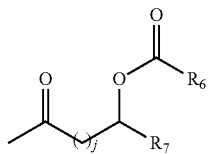

wherein j is an integer from 1 to 5, and R$_6$ and R$_7$ are independently selected from the group of a hydrogen, an optionally substituted $C_{1-20}$ alkyl group, or a pharmacologically acceptable salt thereof; and R$_8$ is a Hydrogen or an optionally substituted $C_1$-$C_{12}$ alkyl group.

In yet another aspect, the present invention provides for the synthesis, composition and use of the Activated Iminium Cations formed by the reaction of natural and synthetic saponin derivatives including, but not limited to, QS-21 (*Quillaja saponaria*), or its derivatives and a transimination nucleophilic catalyst, and their use as adjuvants and immune response modifiers. Preferred catalysts include, but are not limited to, p-aminobenzoic (PABA) acid, p-aminohippuric acid (PAHA), anthranilic acid and derivatives of p-aminobenzoic (PABA) acid, p-aminohippuric acid (PAHA) and anthranilic acid.

Imine Therapeutics as Adjuvants for Vaccine Interventions

*Quillaja saponaria* is a saponin immunologic adjuvant currently under investigation in a number of clinical trials. Recent findings using synthetic QS-21 demonstrate unequivocally that the adjuvant activity of QS-21 resides in these two principal isomeric forms, and not in trace contaminants within the natural extracts. Furthermore, it has been demonstrated that Schiff base adduct formation with the aldehyde at the C4 position on the triterpene is a pre-requisite for adjuvanticity. Modification of the C4 aldehyde eliminates adjuvant activity for antibody stimulation or for induction of cytotoxic T-lymphocytes.

The kinetics of Schiff base formation between the C4 aliphatic aldehyde of saponin derivatives and endobiotic amines of the immune system is slow under physiological conditions. As the adjuvanticity of said saponins is dependent upon Schiff base formation, we contemplate that increasing the rate of Schiff base formation would provide for an increase in the adjuvanticity (efficacy) of said saponins.

In another aspect, the invention provides for novel imine compounds, formed by reacting a transimination nucleophilic catalyst with a saponin derivative, and their pharmacologically acceptable salts. Preferred saponin derivatives include QS-21-Api, and QS-21-Xyl, and synthetic derivatives of QS-21 that form Schiff base adducts with endobiotic biological targets. Preferred catalysts include those that are safe for use in mammals and include, but are not limited to, aniline derivatives and more specifically p-aminobenzoic acid (PABA), p-aminohipporic acid (PAHA), esterified derivatives of p-aminobenzoic acid, anthranilic acid and derivatives of anthranilic acid, including esterified derivatives. Other preferred classes of catalyst include proline, proline derivatives, imidazolidinones, and other primary, secondary, and aromatic amines.

In another aspect, the present invention also provides for a method to increase the rate of reaction between an adjuvant and endobiotic biological amine. In this aspect, a transimination nucleophilic catalyst is co-administered with an adjuvant in order to improve the rate of Schiff base formation between said adjuvant and an endobiotic biological amine. The catalyst is useful to decrease the effective concentration of said adjuvant and thereby useful to mitigate the likelihood of adverse, concentration dependent toxicity. While not wishing to be bound by theory, the authors believe that said catalyst and said adjuvant react in situ to form a more reactive imine or iminium cation, which subsequently undergoes transimination (trans-Schiffization) with the endobiotic amine target at kinetically fast rates. Said catalyst improves the rate of Schiff base adduct formation between said endobiotic biological amine and said adjuvant.

In another aspect, the present invention provides for a method to increase the adjuvanticity of saponin adjuvants whereby said catalyst is co-administered with an immunological adjuvant and a keyhole limpet hemocyanin conjugate vaccine or other classes of subunit antigen vaccines. Said catalyst is co-administered and used to increase the rate of Schiff base adduct formation between the adjuvant and endobiotic target. Use of said catalyst, or combination of catalysts, increases the rate of reaction between said adjuvant and endobiotic biological target. As a consequence of the increase in rate, the effective concentration of aldehyde required to ligate a given amount of protein is dramatically reduced.

The invention also provides compounds of the formula:

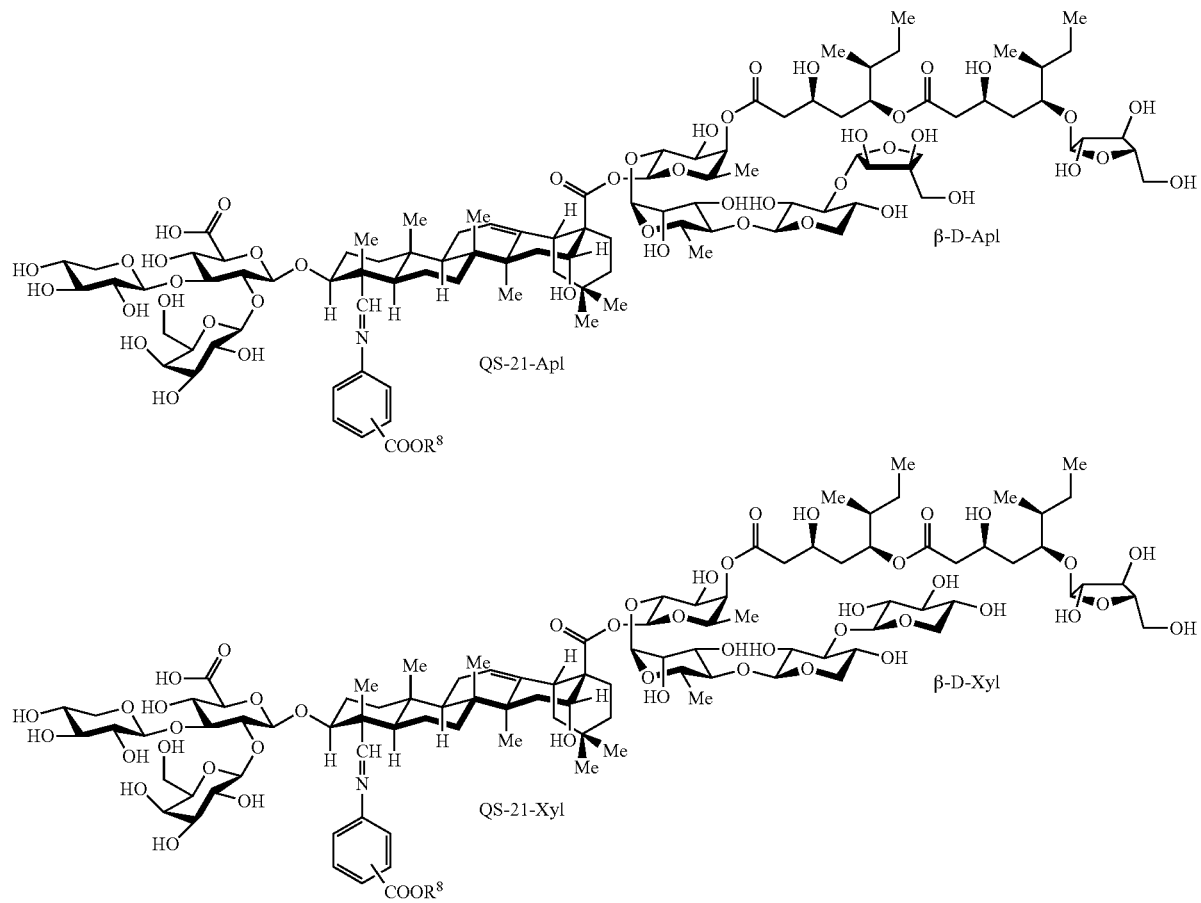

where $R_8$ is a Hydrogen or an optionally substituted $C_1$-$C_{12}$ alkyl group.

Sunless Tanning

Sunless tanners provide an alternative to recreational tanning, but their widespread use is limited by the unsatisfactory performance of the products; a direct result of the poor reactivity of the active ingredients (keto-sugars). The resulting faux tan is slow to develop and the intermediary reaction products are susceptible to degradation under UV radiation, producing harmful reactive oxygen species that have acute and chronic effects.[4,5] The slow development of Melanoidin formation is also problematic for consumers, as the homogeneity of the application remains unknown for several hours post-application.[10]

Current Paradigm—Sunless tanning formulas utilizing dihydroxyacetone (DHA) have been commercially available for 50 years.[11] Recently, combinations of DHA and erythrulose have been utilized to obtain a more favorable end color.[12] DHA and erythrulose are keto-sugars that undergo non-enzymatic glycosylation reactions (Maillard reaction) with epidermal keratin, producing colored pigments that are covalently bound to the outer layers of the epidermis.[2] These colored pigments, collectively referred to as melanoidins, take up to 24 hours to fully develop and are visible for several days, only being removed as the skin sheds.[2-5] The chemical intermediates involved in Melanoidin formation have long lifetimes, and are susceptible to photo-degradation upon exposure to sunlight, producing reactive oxygen species (ROS).[4,5] The ROS are harmful and cause acute and chronic damage to the skin.[4,5] As such, the consumer is advised to avoid sunlight for several hours after application of the sunless tanner.[4-6]

While the complete reaction pathway leading to Melanoidin formation remains unknown, Schiff base adduct formation between the keto-sugar and epidermis is the first reaction in a series of reactions that produce the tanned appearance (faux tan).[13] The current approach is inherently limited, as the rate of reaction between a ketone and epidermal amine is kinetically slow under physiological conditions. The current state of the art remains unsatisfactory and leaves the consumer susceptible to photo-induced free radical formation as the faux tan slowly develops.[1] Furthermore, the slow development of Melanoidin formation leaves the consumer unsure as to the homogeneity of the application.[10] To compensate for the slow development of color, formulators have incorporated visible "tracers" (brown colored pigments) into the delivery vehicles, which allow the consumer to track the application of the formula. The use of these tracers is misleading as the intensity of the resultant faux tan does not correlate with the evenness of tracer distribution. The homogeneity of the resultant faux tan is dependent upon the concentration of keratin in the application area. As different areas of the skin contain varying concentrations of keratin, the resultant faux tan appears uneven. The problem is further compounded by the rapid degradation of the keto-sugar to malodorous by-products and the premature removal of unreacted keto-sugars by absorption, perspiring and normal wear.[4] It would be advantageous to accelerate the rate of reaction between the epidermal amines and keto-sugars, thereby decreasing the lifetime of the photo-unstable chemical intermediates, accelerating the rate of the appearance of the faux tan, eliminating the likelihood for malodor, and decreasing the likelihood for premature removal of the sugar.

Sunless tanners and Turbo-PUVA Therapy—Psoriasis is a chronic autoimmune disease characterized by the formation of red, amorphous skin plaques.[14] The administration of psoralens (oral or topical), combined with UVA phototherapy (PUVA) has been shown to be efficacious at removing the plaques, but the therapeutic benefits are limited by the acute and chronic effects of cumulative exposure to UVA radiation.[2,15] The collateral damage to non-psoriatic skin limits the aggressiveness of the phototherapy, and the overall effectiveness of the strategy.[2,15] Recently, sunless tanners have been used to impart a topical UV-resisting barrier to optimize PUVA (Turbo-PUVA). The melanoidins, covalently bound to epidermal keratin, offer modest levels of UVA protection that correlate with the intensity of the faux tan. As the hyperproliferative psoriatic plaques shed more quickly than unaffected areas, the remaining normal skin is left with a modest level of UV protection during subsequent phototherapeutic treatments.[2] The Turbo-PUVA strategy allows for the administration of higher UVA doses by simultaneously accelerating plaque clearing and protecting the unaffected skin areas. While the clinical utility of Turbo-PUVA has been demonstrated in humans, the utility of the current Turbo-PUVA strategy is limited by the slow development of the faux tan and its very modest UV-protecting ability. Melanoidin formation is exceedingly slow, and much of the applied keto-sugar remains unreacted and wasted. The sunless tanner must be applied over several applications in order to generate a sufficiently "dark" faux tan, and the corresponding UVA protection.

Our approach seeks to enhance the utility of reducing sugars to react with epidermal amines and provide for a safer and improved alternative to sun bathing and indoor tanning. Co-administration of a benign transimination nucleophilic catalyst and keto-sugar, or the isolated imine, provides for a highly reactive iminium cation that subsequently undergoes transimination with epidermal amines at enhanced rates. Upon Schiff base adduct formation the catalyst is regenerated (FIG. 1). We hypothesize that the catalysts will reduce ROS generation and produce melanoidins with enhanced UV-protecting ability. Validation of these hypotheses would significantly advance the development of the AIC approach towards commercialization and provide a strategic technical advantage over current products.

In another aspect, the present invention provides for a method to improve the rate of color change on human skin. In this aspect, a transimination nucleophilic catalyst is co-administered with a reducing sugar and delivered to the skin. The catalyst and reducing sugar react to form a more reactive imine that undergoes transimination with amines of the skin.

Pharmaceutical Compositions

When employed as pharmaceuticals, the imine compounds of this invention are typically administered in the form of a pharmaceutical composition. Such compositions can be prepared in a manner well known in the pharmaceutical art and comprise at least one active complex. In a further embodiment, the pharmaceutical compositions of the invention may comprise one or more of the imine compounds in combination with one or more non-imine compounds, including known compounds. Such combinations yield compositions that exhibit improved effectiveness over like compositions containing the active compounds individually, so that a synergistic effect of the combination is conferred. The exact amounts and proportions of the compounds with respect to each other may vary within the skill of the art.

Generally, the imine compound of this invention is administered in a pharmaceutically effective amount. The amount of the complex actually administered will typically be determined by a physician, in the light of the relevant circumstances, including the condition to be treated, the chosen route of administration, the actual complex administered, the age, weight, and response of the individual patient, the severity of the patient's symptoms, and the like.

The pharmaceutical compositions of this invention can be administered by a variety of routes including by way of non-limiting example, oral, rectal, vaginal, transdermal, subcutaneous, intravenous, intramuscular and intranasal. Depending upon the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in Remington's Pharmaceutical Sciences.

The following formulation examples illustrate representative pharmaceutical compositions of this invention. The present invention, however, is not limited to the following pharmaceutical compositions.

Formulation 1—Tablets

A compound containing an imine compound or a mixture of catalyst(s) and carbonyl molecule of the invention is admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2—Capsules

A compound containing an imine compound or a mixture of catalyst(s) and carbonyl molecule of the invention is admixed as a dry powder with a starch diluent in an approximate 1:1 weight ratio. The mixture is filled into 250 mg capsules (125 mg of active compound per capsule).

Formulation 3—Liquid

A compound containing a an imine compound or a mixture of catalyst(s) and carbonyl molecule of the invention (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound containing an imine compound or a mixture of catalyst(s) and carbonyl molecule of the invention is admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5—Injection

A compound containing a an imine compound or a mixture of catalyst(s) and carbonyl molecule of the invention is dissolved or suspended in a buffered sterile saline injectable aqueous medium to a concentration of approximately 5 mg/ml.

Formulation 6—Topical

Stearyl alcohol (250 g) and a white petrolatum (250 g) are melted at about 75° C. and then a an imine compound or a mixture of catalyst(s) and carbonyl molecule of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present complexes may be used as therapeutic agents for the treatment of conditions in mammals. Accordingly, the complexes and pharmaceutical compositions of this invention find use as therapeutics for treating sickle cell disease and/or treating chronic infections and/or modulating immune response and related conditions in mammals, including humans.

In a method of treatment aspect, this invention provides a method of treating a mammal susceptible to or afflicted with a condition associated with or resulting from chronic infection, genetic disorder, bacterial, viral or fungal attack or infection, which method comprises administering an effective amount of one or more of the pharmaceutical compositions just described to a patient or subject in need.

In additional method of treatment aspects, this invention provides methods of treating a mammal susceptible to or afflicted with a variety of chronic infections, genetic disorders, bacterial, viral or fungal attack or infection, or other infections, The method comprises administering an effective condition-treating or condition-preventing amount of one or more of the pharmaceutical compositions just described to a patient or subject in need.

For the prevention and/or treatment of long-term conditions, such as those associated with persistent viral or microbial conditions, or genetic disorder the regimen for treatment usually stretches over many months or years so oral dosing is preferred for patient convenience and tolerance.

Transdermal doses are generally selected to provide similar or lower blood levels than are achieved using injection doses.

The complexes of this invention can be administered as the sole active agent or they can be administered in combination with other agents, including other active derivatives.

General Synthetic Procedures

The complexes of this invention can be prepared from readily available starting materials using the general methods and procedures described earlier and illustrated schematically in the examples that follow. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The following methods are presented with details as to the preparation of representative imine compounds that have been listed hereinabove. The imine compounds of the invention may be prepared from known or commercially available starting materials and reagents by one skilled in the art of organic synthesis.

Solvents and reagents purchased from commercial sources were used without further purification.

Representative Synthetic Method
Preparation of Imine Compounds

General protocols for the synthesis of imine compounds are shown in Scheme 1. The carbonyl molecule is dissolved in anhydrous alcohol, and to this solution is added an equivalent amount of transimination nucleophilic catalyst. After mixing, a catalytic amount of glacial acetic acid is added and the reaction is mixed at room temperature for several hours. The reaction product can be purified by precipitation or by removal of the alcohol under vacuum. All products are characterized by $^1$HNMR and mass spectrometry.

Example 1

Preparation of 4-((5-(hydroxymethyl)furan-2-yl)methyleneamino)benzoic acid (Termed AIC)

The following non-limiting example represents the synthesis of an imine therapeutic based on the transimination nucleophilic catalyst p-aminobenzoic acid (PABA) and is applicable to a wide number of synthesis' whereby PABA is the catalyst.

To a solution of 5-hydroxy-2-methylfurfural (10 mM) in anhydrous ethanol was added p-aminobenzoic acid (11 mM) in anhydrous ethanol. To this solution was added 50 µL of glacial acetic acid. The solution was mixed at room temperature for 4 h and the off-white precipitate was filtered and washed with cold EtOH to yield the final product in quantitative yields.

Example 2

Preparation of 4-(4-hydroxy-3-methoxybenzylideneamino)benzoic acid

The following non-limiting example represents the synthesis of an imine therapeutic based on the transimination nucleophilic catalyst p-aminobenzoic acid (PABA) and is applicable to a wide number of synthesis' whereby PABA is the catalyst.

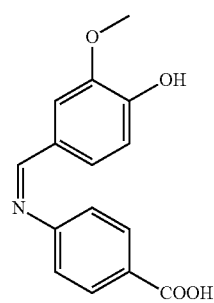 [SMILES: COc1cc(/C=N\c2ccc(C(=O)O)cc2)ccc1O]

To a solution of vanillin (10 mM) in anhydrous ethanol was added p-aminobenzoic acid (11 mM) in anhydrous ethanol. To this solution was added 50 µL of glacial acetic acid. The solution was mixed at room temperature for 4 h and the off-white precipitate was filtered and washed with cold EtOH to yield the final product in quantitative yields.

Example 3

Preparation of 4-(2-hydroxy-3-methoxybenzylideneamino)benzoic acid

The following non-limiting example represents the synthesis of an imine therapeutic based on the transimination nucleophilic catalyst p-aminobenzoic acid (PABA) and is applicable to a wide number of synthesis' whereby PABA is the catalyst.

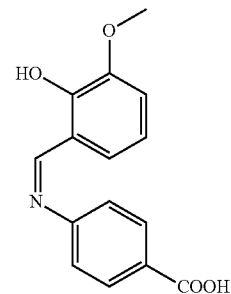 [SMILES: COc1cccc(/C=N\c2ccc(C(=O)O)cc2)c1O]

To a solution of o-vanillin (10 mM) in anhydrous ethanol was added p-aminobenzoic acid (11 mM) in anhydrous ethanol. To this solution was added 50 µL of glacial acetic acid. The solution was mixed at room temperature for 4 h and the off-white precipitate was filtered and washed with cold EtOH to yield the final product in quantitative yields.

Example 4

Preparation of 2-((4-carboxyphenylimino)methyl)-5-hydroxybenzoic acid

The following non-limiting example represents the synthesis of an imine therapeutic based on the transimination nucleophilic catalyst p-aminobenzoic acid (PABA) and is applicable to a wide number of synthesis' whereby PABA is the catalyst.

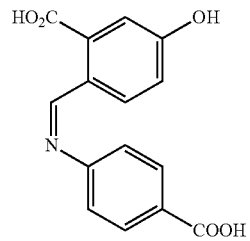

To a solution of 2-formyl-5-hydroxybenzoic acid (10 mM) in anhydrous ethanol was added p-aminobenzoic acid (11 mM) in anhydrous ethanol. To this solution was added 50 µL of glacial acetic acid. The solution was mixed at room temperature for 4 h and the off-white precipitate was filtered and washed with cold EtOH to yield the final product in quantitative yields.

Example 5

Preparation of 4-(4-methoxy-2-(2-(pyridin-4-yl)ethyl)benzylideneamino)benzoic acid The following non-limiting example represents the synthesis of an imine therapeutic based on the transimination nucleophilic catalyst p-aminobenzoic acid (PABA) and is applicable to a wide number of synthesis' whereby PABA is the catalyst.

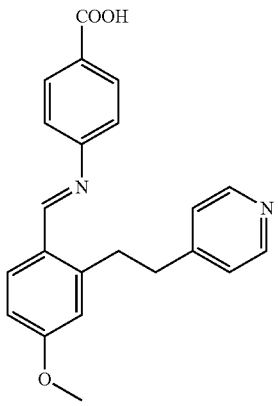 [SMILES: COc1ccc(/C=N/c2ccc(C(=O)O)cc2)c(CCc2ccncc2)c1]

To a solution of 4-methoxy-2-(2-(pyridin-4-yl)ethyl)benzaldehyde (10 mM) in anhydrous ethanol was added p-aminobenzoic acid (11 mM) in anhydrous ethanol. To this solution was added 50 µL of glacial acetic acid. The solution was mixed at room temperature for 4 h and the off-white precipitate was filtered and washed with cold EtOH to yield the final product in quantitative yields.

Example 6

Preparation of 4-(4-methoxy-3-(pyridin-2-ylmethoxy)benzylideneamino)benzoic acid

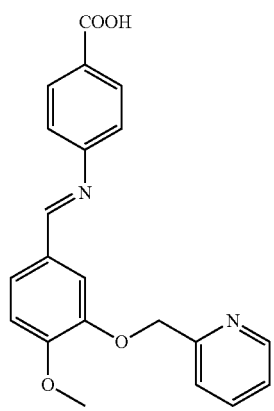 [SMILES: COc1ccc(/C=N/c2ccc(C(=O)O)cc2)cc1OCc1ccccn1]

The following non-limiting example represents the synthesis of an imine therapeutic based on the transimination nucleophilic catalyst p-aminobenzoic acid (PABA) and is applicable to a wide number of synthesis' whereby PABA is the catalyst.

To a solution of 4-methoxy-3-(pyridin-2-ylmethoxy)benzaldehyde (10 mM) in anhydrous ethanol was added p-aminobenzoic acid (11 mM) in anhydrous ethanol. To this solution was added 50 µL of glacial acetic acid. The solution was mixed at room temperature for 4 h and the off-white precipitate was filtered and washed with cold EtOH to yield the final product in quantitative yields.

Example 7

Preparation of 4-(3-methoxy-4-(pyridin-2-ylmethoxy)benzylideneamino)benzoic acid The following non-limiting example represents the synthesis of an imine therapeutic based on the transimination nucleophilic catalyst p-aminobenzoic acid (PABA) and is applicable to a wide number of synthesis' whereby PABA is the catalyst.

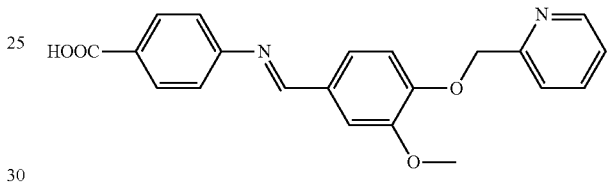

To a solution of 3-methoxy-4-(pyridin-2-ylmethoxy)benzaldehyde (10 mM) in anhydrous ethanol was added p-aminobenzoic acid (11 mM) in anhydrous ethanol. To this solution was added 50 µL of glacial acetic acid. The solution was mixed at room temperature for 4 h and the off-white precipitate was filtered and washed with cold EtOH to yield the final product in quantitative yields.

Example 8

The Oxygen Affinity of Hemoglobin Increases in the Presence of 5HMF and Increasing PABA

TABLE 1

Influence of catalyst concentration on $\Delta P_{50}$ (%) after 1 h at 37° C. PABA Na$^+$ is the sodium salt of p-aminobenzoate (Sigma), 5HMF is 5-hydroxymethyl-2-furfural (Sigma).

| Exp | 5HMF (mM) | PABA Na$^+$ (mM) | $P_{50}$ (mmHg) | $^a\Delta P_{50}$ (%) (mmHg) | $^b n_{50}$ |
|---|---|---|---|---|---|
| A | 1 | — | 14.00 | 7.53 | 2.50 |
| B | 1 | 1 | 10.81 | 28.60 | 1.90 |
| C | 1 | 10 | 9.22 | 39.10 | 1.77 |
| D | 1 | 100 | 6.74 | 55.48 | 2.17 |
| E | 3 | — | 8.21 | 45.78 | 1.73 |
| F | 5 | — | 5.72 | 62.22 | 1.91 |

$^a\Delta P_{50}$ = (P50 control (HbS only) – $P_{50}$ sample)/($P_{50}$ control) expressed as a percentage.
$^b n_{50}$ is the hill coefficient. All samples contain the same concentration of DMSO.

Studies were initiated to explore the relationship between the concentration of PABA and the effect on the oxygen equilibrium curves and $\Delta P_{50}$ of Hb solutions containing 1 mM 5-hydroxymethyl-2-furfural. The oxygen equilibrium curves (OEC) of hemoglobin (1 mg/ml) in phosphate buffer saline pH 7.4 containing 100 mM, 10 mM or 1 mM of the sodium salt of p-aminobenzoate (Sigma) were determined with a Hemox Analyzer (TCS Scientific Corp.). Hemoglobin solutions were incubated at 37° C. for 1 h, in the presence (+) or absence (−) of each compound, as specified in Table 1. In the absence of 5HMF and PABA (Hb control), the OEC of the Hb suspension is a sigmoid curve with a $P_{50}$ value of 15.14 mmHg at 37° C. Pre-incubation of the Hb suspensions (containing 1 mM 5HMF) with increasing concentrations of PABA (Experiments B, C, and D) shifted the position of the OECs towards the left. The shapes of the curves changed from sigmoid to hyperbolic with increasing catalyst concentration, suggesting a decreasing cooperativity and increasing oxygen affinity. The addition of an equimolar amount of PABA increased the efficacy of 5HMF significantly. Increasing the PABA concentration to 10 mM and 100 mM (5HMF constant at 1 mM) increased the oxygen affinity further, but these changes did not impact the oxygen affinity as significantly. The increase in the oxygen affinity was compared with what was observed for increasing concentrations of 5HMF in the absence of PABA (Experiments A, E and F). In these controls, the OEC was shifted left, and the shape of the curve changed from sigmoid to hyperbolic (as with the presence of PABA). The presence of equimolar amounts of 1 mM 5HMF and 1 mM PABA increased the percent $\Delta P_{50}$ value by almost four fold as compared to the change with 1 mM 5HMF alone. Control experiments with solutions of Hb containing 100 mM, 10 mM or 1 mM PABA (no 5HMF) did not shift the OEC or cause a change in the $P_{50}$ value, when compared with the Hb control experiment. The increase in $P_{50}$ of Hb (higher oxygen affinity) in the presence of 5HMF and PABA is a reflection of the generation of AIC generated in situ, which is more reactive with Hb than 5HMF alone.

Example 9

The Imine Therapeutic of Example 1 (AIC) Reacts with Hemoglobin at Kinetically Fast Rates The isolated imine of Example 1, formed by reacting p-aminobenzoic acid and 5-hydroxymethyl furfural, reacts with hemoglobin at faster rates than 5HMF. The therapeutic imine was synthesized according to Example 1. To a solution of purified HbA (1 mg/ml), from an anonymous human donor, in PBS 7.4 was added equivalent amounts of the therapeutic imine of AIC (1 mM), or 5HMF (1 mM). The HbA solutions show a new peak (~7.1 min) on cation-exchange HPLC (Table 2) that elutes prior to the unmodified HbA peak (~8.2 min). The new peak represents the 5HMF/HbS formed between 5HMF and HbA and can be quantified by integration of the representative peaks. (6,7) Consistent with our hypothesis, the therapeutic imine of Example 1. modifies HbA at significantly enhanced rates compared to 5HMF at identical concentrations. The initial rate of Schiff base adduct formation between the therapeutic imine and HbA is nearly 10 times faster than the rate of formation between 5HMF and HbA, as determined by cation-exchange HPLC at room temperature. After 30 min at room temperature, the 1 mM AIC solution resulted in ~32% of the desired Hb adduct, compared to just 6% in the 1 mM 5HMF solution (Table 2). Control studies (PABA only) did not show a new peak by HPLC.

Example 10

The Therapeutic Imine AIC Forms 5HMF/HbS Adducts Ex Vivo at Faster Rates Compared to 5HMF Alone To aliquots of whole blood (100 μL), from the BERKγM mouse, was added either AIC (Example 1) (5 mM) or 5HMF (5 mM). The blood was incubated for 1 h at 37° C. with shaking and aliquots were washed, lysed and analyzed by HPLC as described above. Consistent with our hypothesis, AIC permeates the erythrocyte membrane and forms 5HMF/HbS adducts at significantly enhanced rates compared to 5HMF at identical concentrations. The initial rate of 5HMF/HbS adduct formation using AIC (measured after 10 min) is significantly faster than the rate of formation using 5HMF alone. After 30 min at 37° C. the 5 mM AIC solution resulted in formation of 50% of the desired 5HMF/HbS adduct, compared to 27% in the 5 mM 5HMF solution (FIG. 1). Negative controls (PABA only) did not show a new peak by HPLC.

Example 11

AIC is More Stable to Air, Light and Moisture as Compared to 5HMF

The commercial-scale production, distribution and stability of 5HMF, a hygroscopic off-white solid, may be costly as the compound is highly susceptible to degradation upon exposure to air, light and moisture (21). The AIC, isolated as a white powder (salt), as described above, is significantly more stable in terms of its degradation. To quantify the differences in stability, 500 mg of AIC or 5HMF were placed in a controlled humidity chamber and exposed to light at 22° C. for a period of 2 wks. The 5HMF sample becomes yellow after 24 h, and has several new peaks in the $^1$HNMR spectra and HPLC chromatogram. After 3 days, the 5HMF sample has undergone significant chemical changes, as indicated by a new chemical shifts in the aliphatic region of the $^1$HNMR spectra, and significant changes in the HPLC chromatogram. The AIC did not exhibit a noticeable color change over the 2-week evaluation period, and no changes in the $^1$HNMR spectra and HPLC chromatogram were observed.

Example 12

Figure 2:
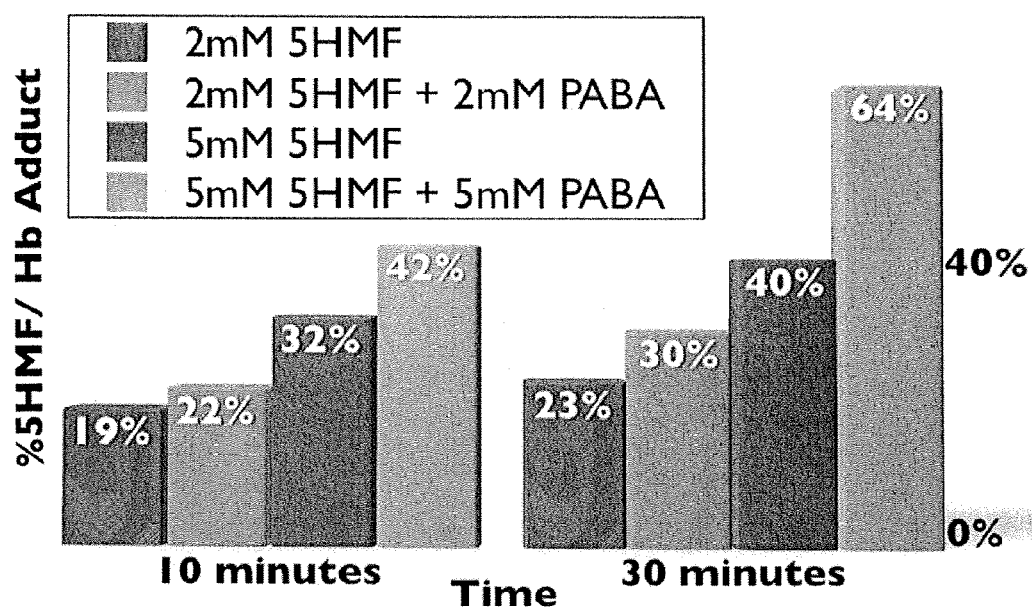
FIG. 2 shows the Mixing of PABA and 5HMF ex vivo. Graph showing the percent of 5HMF/HbS adduct formed in whole blood taken from a BERKγM mouse in the presence of 2 mM 5HMF (red), 2 mM 5HMF+2 mM PABA (green), 5 mM 5HMF (purple) or 5 mM 5HMF+5 mM PABA. The amount of 5HMF/HbS adduct formed is significantly increased in the presence of equimolar PABA.

Mixtures of PABA and 5HMF Enhance the Rate of Formation of 5HMF/HbS Adducts Ex Vivo Studies were initiated to explore the impact of mixing equimolar concentrations of PABA and 5HMF on the rate of 5HMF/HbS adduct formation in whole blood from a BERKγM transgenic mouse. To aliquots of whole blood (100 μL) was added either 5HMF (2 mM or 5 mM), the sodium salt of PABA (2 mM or 5 mM), or equimolar concentrations of PABA/5HMF (2 mM or 5 mM). The blood was incubated for 1 h at 37° C. in a shaking water bath and aliquots were washed, lysed and analyzed by cation-exchange chromatography as described above. The rate enhancements are not optimized in these experiments, and additional experiments to account for the differences in rates of transport across the RBC membrane will be performed during Phase II SBIR studies. However, after 30 minutes at 37° C., the whole blood containing equimolar PABA/5HMF (5 mM) resulted in 64% of the desired 5HMF/HbS adduct compared to just 40% with the use of 5 mM 5HMF alone. Equimolar solutions of 2 mM PABA/5HMF resulted in 30% of the 5HMF/HbS adduct being formed, compared to just 23% when using 2 mM 5HMF alone (FIG. 2). Control experiments with PABA only did not result in any adduct formation. These results are encouraging and validate the hypothesis that co-administration of PABA is useful to decrease the concentration of 5HMF needed to modify red blood cells ex vivo; the molecular basis of the proposed anti-sickling therapeutic approach.

Example 13

Figure 3:
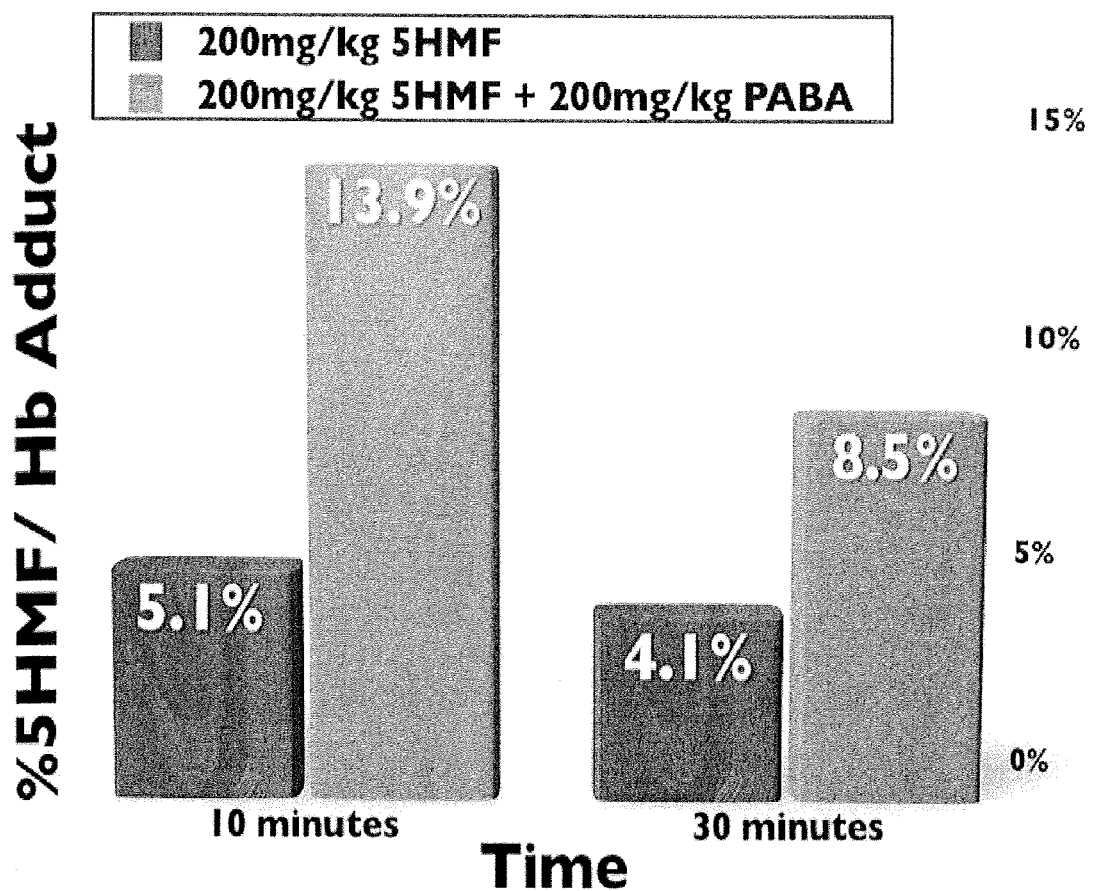
FIG. 3 shows the In vivo intravenous administration of 5HMF (red bars) or PABA and 5HMF (blue bars). All reagent concentrations were 200 mg/kg. Mice injected with 5HMF alone were lethargic and exhibited noticeable changes in behavior, while mice injected with PABA/5HMF behaved as normal.

Co-Administration of PABA and 5HMF Enhances the Rate of Formation of 5HMF/HbS Adducts In Vivo BERK M mice were injected (intravenous) with solutions containing either 5HMF (200 mg/kg) or 5HMF (200 mg/kg) and the sodium salt of PABA (200 mg/kg). The mice that were injected with only 200 mg/kg 5HMF became lethargic and exhibited noticeable changes in behavior, while mice that were injected with solutions of 5HMF/PABA were active as normal. Higher concentrations of 5HMF alone (300-500 mg/kg) caused mice to convulse and die, while co-administration of PABA/5HMF did not have this effect. To assess of 5HMF/HbS adduct formation, aliquots of blood were taken at 10 and 30 min, and immediately washed, lysed and subjected to HPLC as previously described. The initial rate of 5HMF/HbS adduct formation (measured after 10 min) is significantly faster than the rate of formation using 5HMF alone. The initial rate of 5HMF/HbS adduct formation in experiments where PABA was co-administered (measured after 10 min) is significantly faster than the rate of formation using 5HMF alone. After 10 min, mice injected with PABA/5HMF had almost 3x the amount of 5HMF/HbS adduct formed (13.9% 5HMF/HbS adduct) when compared to control experiments with 5HMF alone (5.1% 5HMF/HbS adduct). After 30 min, the amount of 5HMF/HbS adduct decreased to 8.5% and 4.1% respectively (FIG. 3). The conditions in this experiment were not optimized and we attribute the decrease in 5HMF/HbS adduct to the method of administration.

Example 14

Figure 4:
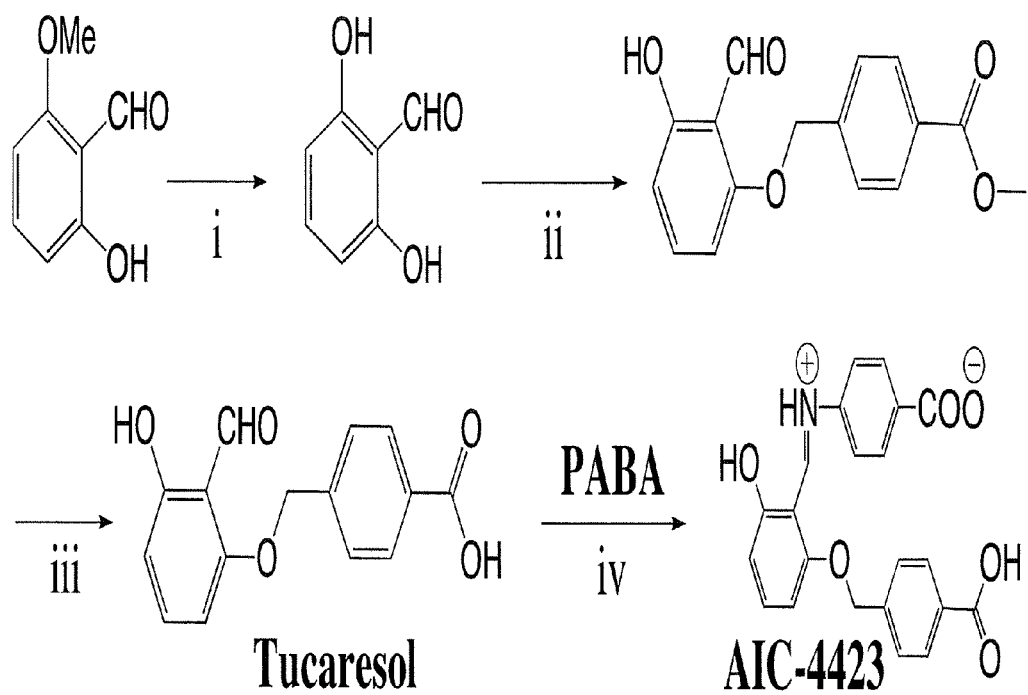
FIG. 4 shows the synthesis of Tucaresol and AIC-4423. The following conditions were used in the synthesis: (i) AlCl3/Benzene 5 h, (ii) methyl 4-(bromomethyl) benzoate, $Cs_2CO_3$, anhydrous DMF, (iii) 1M NaOH (aq), (iv) p-aminobenzoic acid/anhydrous EtOH.

Synthesis of AIC-4423 Synthesis (FIG. 4)

AIC-4423 was synthesized by inexpensive procedures developed in our laboratory (FIG. 4). Tucaresol (10 mM) and p-aminobenzoic acid (11 mM) was mixed in EtOH at room temperature with a catalytic amount of glacial acetic acid. After 4 h at room temperature, AIC-4423 was precipitated as a white solid, washed with ethanol and characterized by $^1$HNMR and LCMS.

Example 15

Figure 5:
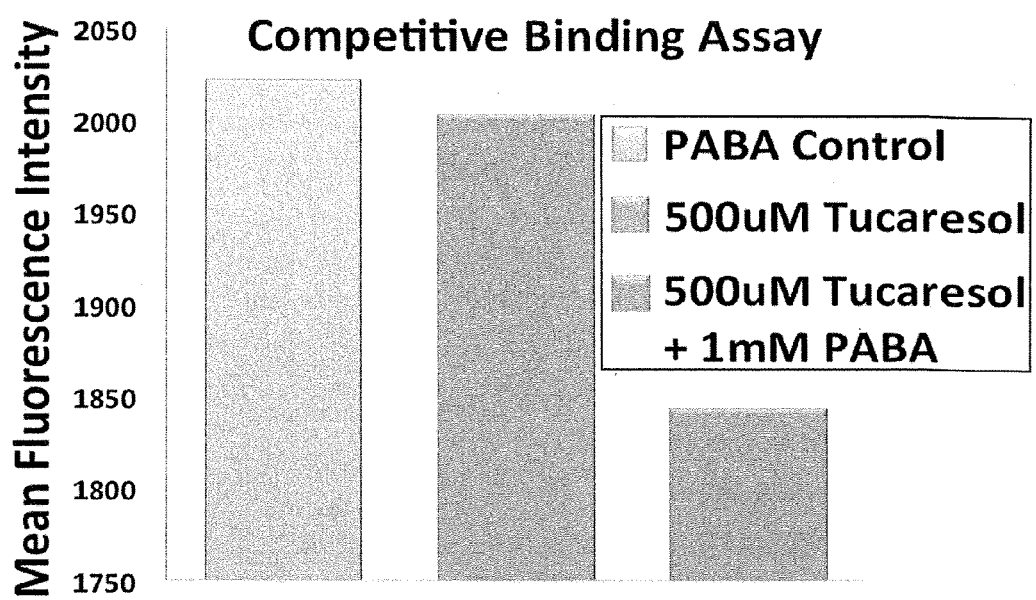
FIG. 5 shows a competitive binding assay demonstrating the influence of 1 mM PABA to accelerate the rate of Schiff base adduct formation between T-cell surface amines and Tucaresol. The mean fluorescence intensity is inversely proportional to the rate and degree of Tucaresol/T-cell adduct formation. As expected, mixtures of 1 mM PABA and 500 μM Tucaresol (red, right) significantly decreased the mean fluorescence intensity of the T-cells, as compared to incubation with 500 μM Tucaresol alone (blue, middle) and the T-cell control experiment (orange, left) where no Tucaresol was incubated with the T-cells.

PABA Enhances the Rate and Degree of Schiff Base Adduct Formation Between Tucaresol and T-Cells The central hypothesis of our approach involves utilizing PABA to increase the rate of Schiff base formation between Tucaresol and T-cells in order to minimize the concentration of Tucaresol required for efficacy. We used an established competitive covalent ligation assay (2) to examine the influence of PABA on the rate and degree of Schiff base-adduct formation between Tucaresol and T-cells isolated from the spleens of Balb/c male mice. In this assay, the degree of Tucaresol/T-cell adduct formation is inversely proportional to the mean fluorescence intensity (as visualized by ligation with S-NHS-biotin and FITC-avidin). T-cells were incubated for 30 min with 500 µM Tucaresol only (blue column, FIG. 5), 1 mM PABA only (orange column, FIG. 5) or a mixture of 500 µM Tucaresol and 1 mM PABA (red column, FIG. 5) at 37° C. After 30 min, the reducing agent NaCNBH$_3$ was added to selectively reduce Schiff base adducts (chemically trapping the Tucaresol/T-cell adduct). Washed cells were exposed for 1 h to 12.5 µM S-NHS-biotin (Pierce Rockford, Ill.) to ligate unreacted free surface amino groups. After washing, cells were exposed to excess fluorescent avidin (FITC-avidin) (Pierce), fixed and visualized using flow cytometry. As expected, cells that were treated with a mixture of PABA/Tucaresol were significantly less fluorescent than cells that were treated with 500 µM Tucaresol alone, indicating that the presence of 1 mM PABA increased the relative rate and degree of Schiff base adduct formation between Tucaresol and T-cell amines. Cells that had been treated with only 500 µM Tucaresol, were similar in fluorescent intensity to cells treated with only 1 mM PABA (negative control), which did not exhibit a change in mean fluorescent intensity as compared to untreated cells (not shown).

Example 16

PABA Enhances the Rate of Melanoidin Formation In Vitro

Figure 6:
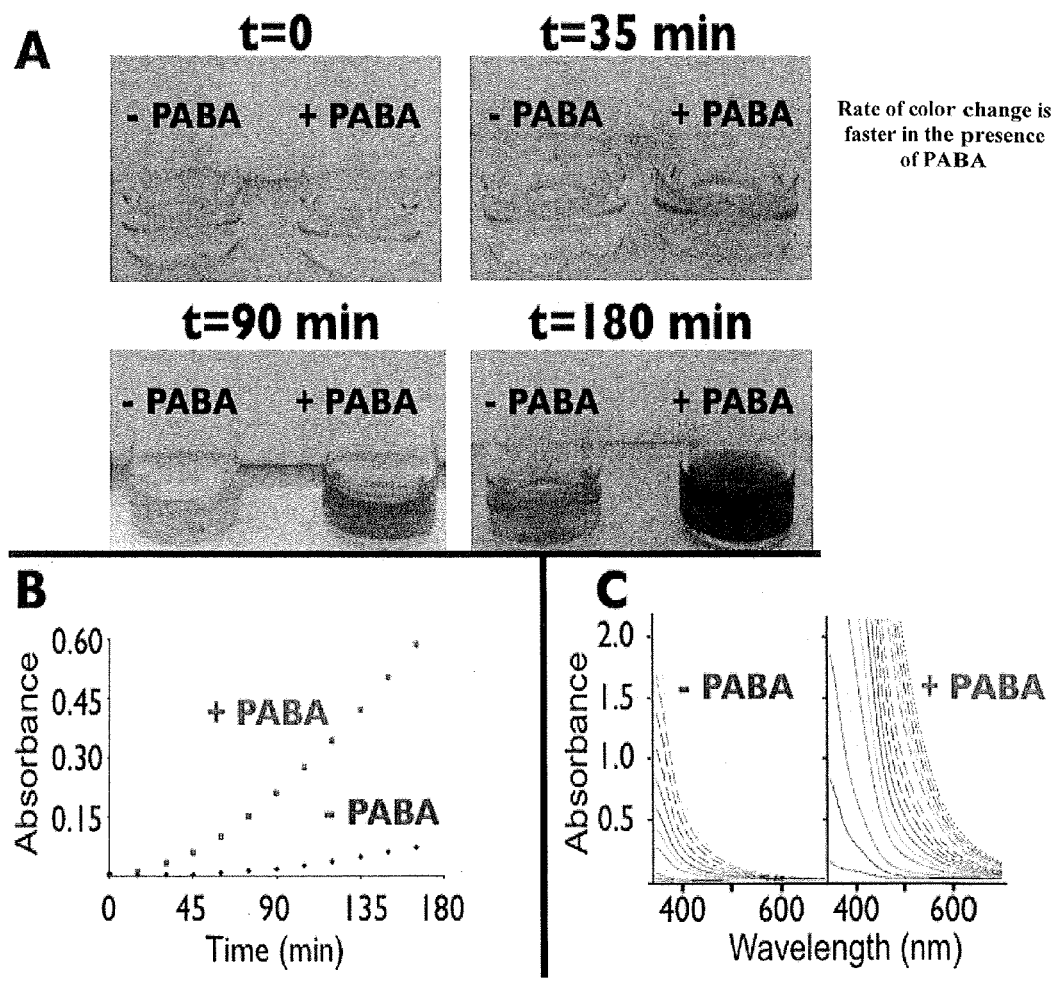
FIG. 6 shows (A) Qualitative assessment of the rate of melanoidin formation in solutions of glycine (6%) and DHA (6%) over time, in the presence (+) or absence (−) of 1% PABA. (B) Quantitative evaluation of the increase in absorbance at 450 nm of solutions of glycine (6%) and DHA (6%) in the presence (+) or absence (−) of 1% PABA. (C) UV-Vis spectrum showing the changes in absorbance (measured every 15 min) from 350-700 nm over time. All experiments were conducted at 32° C.

Low concentrations of the transimination nucleophilic catalyst (PABA) significantly increase the rate at which melanoidin formation occurs in vitro, as determined by the (1) qualitative rate of color change (FIG. 3A) and (2) quantitative change in the UV-VIS spectrum (FIG. 3B, 3C). Solutions of glycine (6%) and DHA (6%) in 100 mM NH$_4$OAc buffer pH 5.5 were incubated in the presence (+) and absence (−) of the sodium salt of PABA (1%) at 32° C. In the presence of 1% PABA, the solutions darkened at faster rates as compared to negative controls (no PABA). Control solutions containing only PABA and DHA (no glycine) did not exhibit significant color changes over the course of the experiment. The UV-Vis spectrum changed more rapidly in the presence of PABA (FIG. 6B, 6C), and the changes in the absorbance spectrum can be used to compare the relative rates of melanoidin formation.

Example 17

PABA Enhances the Rate of Melanoidin Formation In Vivo

Figure 7:
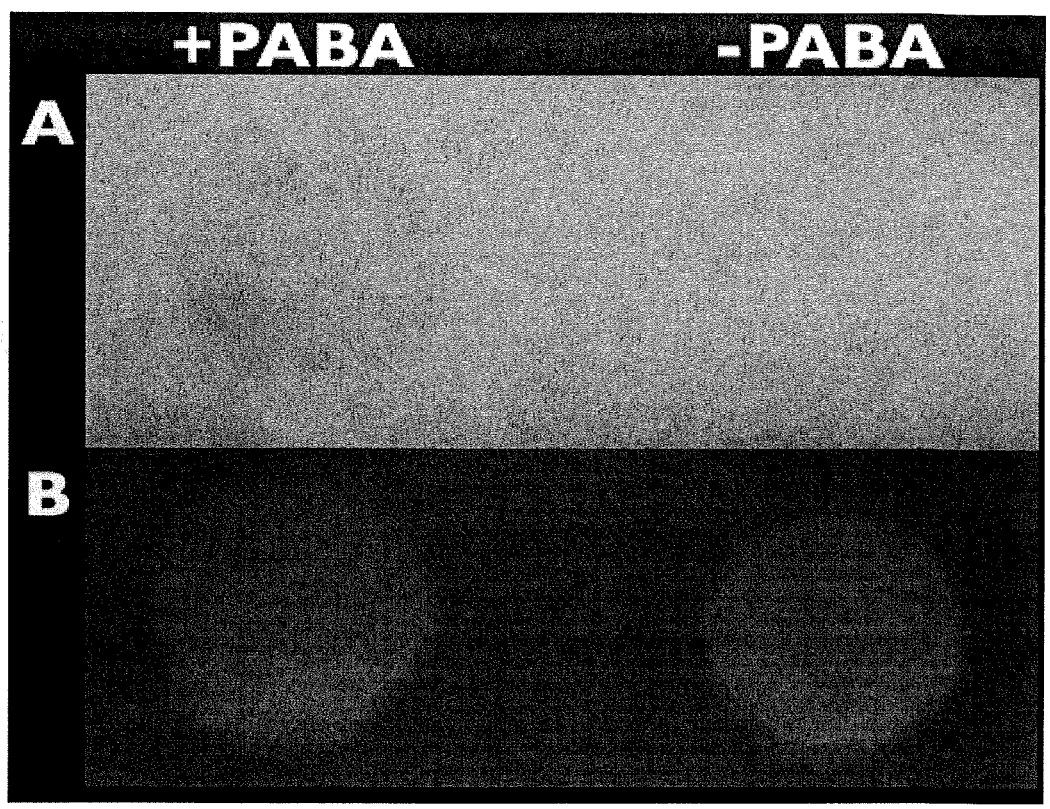
FIG. 7 shows a qualitative assessment of the rate of melanoidin formation in vivo under (A) natural light and (B) UV light, in the presence (+) or absence (−) of 0.25% PABA (t=65 min). Melanoidins appear faster using the +PABA formula and the emission appears to be red-shifted as compared to the area where the −PABA formula was applied.
Figure 8:
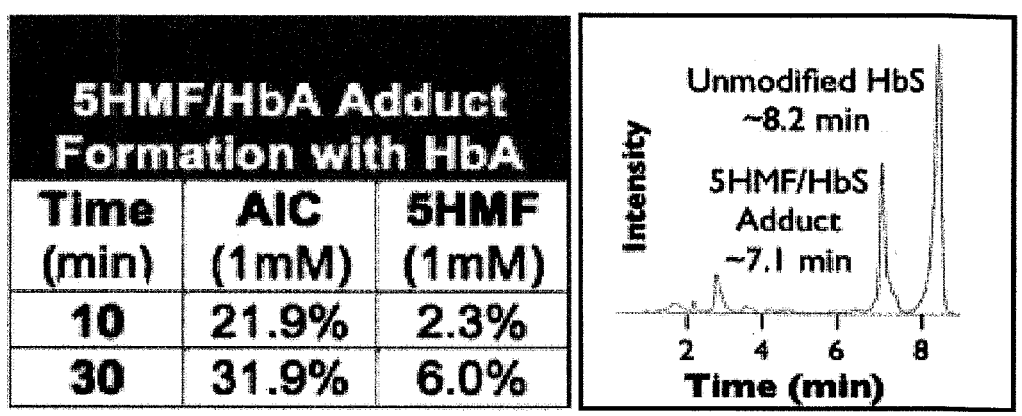
FIG. 8. Table 2. (Left Table). Table showing the percent 5HMF/HbA adduct in the presence of 1 mM AIC or 1 mM 5HMF. The AIC forms 5HMF/HbA adducts at significantly enhanced rates. (Right). Representative cation exchange HPLC chromatogram (410 nm) of hemoglobin that had been incubated with the AIC or 5HMF. A new peak corresponding to the 5HMF/HbA adduct elutes at ~7.1 minutes. Unmodified hemoglobin elutes at ~8.2 min.

The central hypothesis of our strategy was validated in a clinical setting at AMA Laboratories Inc. (New City, N.Y.) where preliminary experiments have established that low concentrations of transimination nucleophilic catalyst (PABA, OABA, Menthyl-o-aminobenzoate, 3-hexen-1-yl anthranilate, methyl anthranilate, ethyl anthranilate, or butyl anthranilate) significantly increase the rate at which melanoidin formation occurs on human skin.[28] The strategy is exemplified in FIG. 7, where solutions of 5% DHA$_{(aq)}$ (+/−PABA) were prepared and 25 µL applied to a pre-defined area (5.1 cm$^2$) on the inner left arm of 3 subjects. The application areas were allowed to dry for 5 min and were monitored for 14 days, with photographs taken throughout. The subjects were asked not to bathe for the first 24 h. The application area where the +PABA solution was applied exhibited noticeable color change within ~15 min. The application area where the control solution (−PABA) was applied did not noticeably darken for ~1 h. Significant differences in the appearance of the application areas were noticeable during the study, and no adverse reactions of any kind were observed. Throughout the study, the color change in the +PABA application area was more homogenous and appeared more "natural" in color (as determined qualitatively by the 3 subjects). Furthermore, the +PABA areas faded more evenly, did not produce detectable malodor and did not exhibit "streaking", as was observed on all 3 panelists in the −PABA application areas. The preliminary results of these experiments are promising, and we plan to expand the study to incorporate a larger, statistically significant panel during phase II SBIR studies.

REFERENCES

References for the Sickle Cell Disease Section

1. Smith, W. R. Pain in sickle cell disease: the future of acute treatment. *Expert Rev. Hematol.* 4, 237-239, 2011.
2. Sophie Lanzkron, MD; John J. Strouse, MD; Renee Wilson, MSc; Mary Catherine Beach, MD, MPH; Carlton Haywood, MA; HaeSong Park, MD, MPH; Catherine Witkop, MD, MPH; Eric B. Bass, MD, MPH; and Jodi B. Segal, MD, MPH. Systemic Review: Hydroxyurea for the Treatment of Adults with Sickle Cell Disease. *Ann Intern Med.,* 148, 939-955, 2008.
3. Teresa L. Kauf, Thomas D. Coates, Liu Huazhi, Nikita Mody-Patel, and Abraham G. Hartzema. The cost of health care for children and adults with sickle cell disease. *Am. J. Hematol.* 84, 323-327, 2009.
4. Ballas, S. K. Pain Management of Sickle Cell Disease. *Hematology/oncology Clinics of North America,* 19, 785-802, 2005.
5. Abboud, M. R.; Musallam, K. M. Sickle Cell Disease at the Dawn of the Molecular Era. *Hemoglobin,* 33, S93-S106, 2009.
6. Safo, M. K.; Abdulmalik, O.; Danso-Danquah, R.; Burnett, J. C.; Nokuri, S.; Joshi, G. S.; Musayev, F. N.; Asakura, T; Abraham, D. J. Structural Baseis for the Potent Antisickling Effect of a Novel Class of Five-Membered Heterocyclic Aldehydic Compounds. *J Med Chem,* 47, 4665-4676, 2004.
7. Adulmalik, O.; Safo, M. K.; Chen, Q.; Yang, J.; Brugnara, C.; Ohene-Frempong, K.; Abraham, D. J.; Asakura, T. 5-hydroxymethyl-2-furfural modifies intracellular sickle haemoglobin and inhibits sickling of red blood cells. *British Journal of Haematology,* 128, 552-561, 2005.
8. Web. 31 Jul. 2011. <http://clinicaltrials.gov/ct2/results?term=sickle+cell>.
9. "AesRx—News." *AesRx—Biopharmaceutical Company Targeting Sickle Cell Disease.* Web. 31 Jul. 2011. <http://www.aesrx.com/news.html>.
10. Gentry, A. Pharmaceutical Stability Testing To Support Global Markets. *Biotechnology: Pharmaceutical Aspects,* 4, 221-228, 2010
11. Arnett, E. M.; Quirk, R. P. Larsen, J. W. Weak bases in strong acids. IV. Basicity scale for carbonyl compounds based on heats of ionization in fluorosulfuric acid. *J. Am. Chem. Soc.,* 92, 3977-3984, 1970.
12. Dirksen, A.; Hackeng, T. M; Dawson, P. E. Nucleophilic Catalysis of Oxime Ligation. *Angew Chem Int Ed,* 45, 7581-7584, 2006.
13. Dirksen, A.; Dirksen, S.; Hackeng, T. M., Dawson, P. E. Nucleophilic Catalysis of Hydrazone Formation and Transimination: Implications for Dynamic Covalent Chemistry. *J. Am. Chem. Soc,* 128, 15602-15603, 2006.
14. Kirksen, A.; Dawson, P. E. Rapid Oxime and Hydrazone Ligations with Aromatic Aldehydes for Biomolecular Labeling. *Bioconjugate Chem,* 19, 2543-2548, 2008.
15. R. J. Hoagland, Para-aminobenzoic acid in the treatment of acute rheumatic fever. *Am. J. Med.,* 9, 272-274, 1950.
16. Wang, H.; Vath, G. M.; Kawamura, A.; Bates, C. A.; Sim, E.; Hanna, P. E.; Wagner, C. R. Over-expression, Purification, and Characterization of Recombinant Human Arylamine N-Acetyltransferase. *Protein J,* 24, 65-77, 2005.
17. Xavier, S., MacDonald, S., Roth, J., Caunt, M., Akalu, A., Morais, D., Buckley, M. T., Liebes, L., Formenti, S. C., and Brooks, P. C. The vitamin-like dietary supplement para-Aminobenzoic acid (PABA) enhances the anti-tumor activity of ionizing radiation. IJROBP 65: 517-527, 2006.
18. Keshavarz-Valian H; Alger N E; Boissonneault G. A. Effects of p-Aminobenzoic Acid, Methionine, Threonine and Protein Levels on Susceptibility of Mice to *Plasmodium berghei. The Journal of Nutrition,* 115, 1613-1620, 1985.
19. Mandell G L and Petri W A. Antimicrobial Agents (Continued). In: Hardman J G, Limbird L, Molinoff P B, Ruddon R W, and Goodman Gilman A (eds.), Goodman & Gilman's The Pharmacological basis of Therapeutics, 9th edition, pp. 1058. New York: McGraw-Hill, 1996.
20. Jencks, William P. *Catalysis in chemistry and enzymology.* New York: Dover, 1987. Print.
21. Kuster, B. F. M. 5-Hydroxymethylfurfural (HMF). A Review Focusing on its Manufacture. *Starch,* 42, 314-321, 1990.
22. Paszty, C., Brion, C. M., Manci, E., Witkowska, H. E., Stevens, M. E., Mohandas, N., and Rubin, E. M. Transgenic knockout mice with exclusively human sickle hemoglobin and sickle cell disease [see comments]. Science. 278:876-878, 1997.
23. Fabry, M. E., Suzuka, S. M., Weinberg, R. S., Lawrence, C., Factor, S. M., Gilman, J. G., Costantini, F., and Nagel, R. L. Second generation knockout sickle mice: the effect of HbF. Blood 97:410-418, 2001.
24. Renato S. Gonçalves, Patrícia V. Abdelnur, Vanessa G. Santos, Rosineide C. Simas, Marcos N. Eberlin, Alviclér Magalhães and Eduardo R. Pérez González. Synthesis of potentially bioactive PABA-related N-(aminoalkyl)lactamic amino acids and esters via selective SNAr reactions. *Amino Acids,* 40, 197-204, 2010.
25. Amber F Hoggatt, Jonathan Hoggatt, Meghan Honerlaw, and Louis M Pelus A Spoonful of Sugar Helps the Medicine Go Down: A Novel Technique to Improve Oral Gavage in Mice. *J Am Assoc Lab Anim Sci,* 49, 329-334, 2010.
26. Erkkil, A.; Majander, I.; Pihko, P. M. Iminium Catalysis. *Chemical Reviews,* 107, 5416-5470, 2007.
27. Zaugg, O. H.; Walder, J. A., Klotz, I. M. Schiff Base Adducts of Hemoglobin. The *Journal of Biological Chemistry,* 23, 8542-8548, 1977.
28. Janzowski, C.; Glaab, V.; Samimi, E.; Schlatter, J.; Eisenbrand, G. 5-Hydroxymethylfurfural: assessment of mutagenicity, DNA-damaging potential and reactivity towards cellular glutathione. *Food and Chemical Toxicology,* 38, 801-809, 2000.
29. Nagababu, E.; Fabry, M. E.; Nagel, R. L.; Rifkind, J. M., Heme degradation and oxidative stress in murine models for hemoglobinopathies: thalassemia, sickle cell disease and hemoglobin C disease. *Blood Cells Mol Dis,* 41, 60-68, 2008.
30. Sandhya Xavier Ph.D., Shannon MacDonald M.D., Jennifer Roth B.S., Maresa Caunt B.S., Abebe Akalu Ph.D., Danielle Morais B.S., Michael T. Buckley M.S., Leonard Liebes Ph.D., Silvia C. Formenti M.D. and Peter C. Brooks Ph.D. The vitamin-like dietary supplement para-aminobenzoic acid enhances the antitumor activity of ionizing radiation. *International Journal of Radiation Oncology*Biology*Physics,* 65, 517-527, 2006.
31. Kaul, D. K. and Hebbel, R. P. Hypoxia/reoxygenation causes inflammatory response in transgenic sickle mice but not in normal mice [see comments]. J. Clin. Invest 106: 411-420, 2000.

32. Kaul, D. K., Liu, X. D., Chang, H. Y., Nagel, R. L., and Fabry, M. E. Effect of fetal hemoglobin on microvascular regulation in sickle transgenic-knockout mice. J. Clin. Invest 114:1136-1145, 2004.
33. Kaul, D. K., Zhang, X., Dasgupta, T., and Fabry, M. E. Arginine therapy of transgenic-knockout sickle mice improves microvascular function by reducing non-nitric oxide vasodilators, hemolysis, and oxidative stress. Am. J. Physiol Heart Circ. Physiol 295:H39-H47, 2008.
34. Hebbel, R. P., Osarogiagbon, R., and Kaul, D. The endothelial biology of sickle cell disease: inflammation and a chronic vasculopathy. Microcirculation. 11:129-151, 2004.
35. Dasgupta, T., Hebbel, R. P., and Kaul, D. K. Protective effect of arginine on oxidative stress in transgenic sickle mouse models. Free Radic. Biol. Med. 41:1771-1780, 2006.
36. Dasgupta, T., Fabry, M. E., and Kaul, D. K. Antisickling property of fetal hemoglobin enhances nitric oxide bioavailability and ameliorates organ oxidative stress in transgenic-knockout sickle mice. Am J Physiol Regul. Integr. Comp Physiol 298:R394-R402, 2010.
37. Kaul, D. K., Kollander, R., Mahaseth, H., Liu, X. D., Solovey, A., Belcher, J., Kelm, R. J., Vercellotti, G. M., and Hebbel, R. P. Robust vascular protective effect of hydroxamic Acid derivatives in a sickle mouse model of inflammation. Microcirculation. 13:489-497, 2006.
38. Kaul, D. K., Fabry, M. E., Costantini, F., Rubin, E. M., and Nagel, R. L. In vivo demonstration of red cell-endothelial interaction, sickling and altered microvascular response to oxygen in the sickle transgenic mouse. J. Clin. Invest. 96:2845-2853, 1995.
39. "WHO|Sickle-cell Disease and Other Haemoglobin Disorders." Web. 31 Jul. 2011. <http://www.who.int/mediacentre/factsheets/fs308/en/index.html>.
40. Charles T. Quinn, Zora R. Rogers, Timothy L. McCavit, and George R. Buchanan. Improved survival of children and adolescents with sickle cell disease. *Blood*, 115, 3447-3452, 2010.
41. Taylor L E, Stotts N A, Humphreys J, Treadwell M J, Miaskowski C. A Review of the Literature on the Multiple Dimensions of Chronic Pain in Adults with Sickle Cell Disease. *Journal of Pain and Symptom Management*, 416-435, 2010.
42. David C. Brousseau, MD, MS; Pamela L. Owens, PhD; Andrew L. Mosso, MS; Julie A. Panepinto, MD, MSPH; Claudia A. Steiner, MD, MPH. Acute Care utilization and Rehospitalizations for Sickle Cell Disease. *JAMA*, 303, 1288-1294, 2010.
43. Mayer M L, Konrad T R, Dvorak C C. Hospital resource utilization among patients with sickle cell disease. *J Health Care Poor Underserved*, 14, 122-35, 2003.
44. Chaojie Zhang, Xiang Li, Lurong Lian, Qiukan Chen, Osheiza Abdulmalik, Vasco Vassilev, Ching-San Lai and Toshio Asakura, Anti-sickling effect of MX-1520, a prodrug of vanillin: an in vivo study using rodents. *British Journal of Haematology*, 125, 788-795, 2004.

References from Sections Small Molecule Immunomodulators for HIV and Imine Therapeutics as Adjuvants for Vaccine Interventions 1. UNAIDS Report On the Global AIDS Epidemic, 2010. ISBN 978-92-9173-871-7
2. Rhodes, J.; Chen, H.; Hall, S. R.; Beesley, J. E.; Jenkings, D. C; Collins, P.; Zheng, B. *Nature* 1995. 377, 71-75.
3. Rhodes, *J Clin Exp Immunol* 2002. 130, 363-369.
4. Hall, S. R.; Rhodes, *J. Immunology* 2001. 104, 50-57.
5. Clerici, Mario; Cogliati, Marta; Rizzardini, Giuliano; Colombo, Fulvia; Fossati, Sabrina; Rhodes, John; Bray, Dorothy; Piconi, Stefania. *Clinical Immunology* 2000. 97, 211-220.
6. Bandera, Alessandra; Marchetti, Giulia; Gori, Andrea. *Expert Opin. Ther. Patents* 2005. 15, 1115-1131.
7. Gori, Andrea; Trabattoni, Dania; Bandera, Alessandra; Saresella, Marina; Marchetti, Giulia; Gazzola, Lidia; Biasin, Mara; Rhodes, John; McDade, Hugh; Panebianco, Ruggero; Galli, Massimo; Moroni, Mauro; Ferrante, Pasquale; Thomas, Nicola; Franzetti, Fabio; Bray, Dorothy; Clerici, Mario. *Antiviral Therapy* 2004. 9, 603-614.
8. Bogdanovic, S.; Langlands, B. *Immunomodulators: Therapeutic Needs, Pipelines & Prospects*. 2007
9. Dirksen, A.; Hackeng, T. M; Dawson, P. E. *Angew Chem Int Ed* 2006. 45, 7581-7584.
10. Dirksen, A.; Dirksen, S.; Hackeng, T. M., Dawson, P. E. *J. Am. Chem. Soc* 2006, 128, 15602-15603.
11. Kirksen, A.; Dawson, P. E. *Bioconjugate Chem* 2008, 19, 2543-2548.
12. R. J. Hoagland. *Am. J. Med.*, 9, 272-274, 1950.
13. Wang, H.; Vath, G. M.; Kawamura, A.; Bates, C. A.; Sim, E.; Hanna, P. E.; Wagner, C. R. *Protein J*, 24, 65-77, 2005.
14. Xavier, S., MacDonald, S., Roth, J., Caunt, M., Akalu, A., Morais, D., Buckley, M. T., Liebes, L., Formenti, S. C., and Brooks, P. C. IJROBP 65: 517-527, 2006.
15. Keshavarz-Valian H; Alger N E; Boissonneault G. A. *The Journal of Nutrition*, 115, 1613-1620, 1985.
16. Mandell G L and Petri W A. Antimicrobial Agents (Continued). In: Hardman J G, Limbird L, Molinoff P B, Ruddon R W, and Goodman Gilman A (eds.), Goodman & Gilman's The Pharmacological basis of Therapeutics, 9th edition, pp. 1058. New York: McGraw-Hill, 1996.
17. Jencks, William P. *Catalysis in chemistry and enzymology*. New York: Dover, 1987. Print.
18. Zacharie, B.; Attardo G.; Barriault, N.; Penney, C. *J. Chem. Soc., Perkin Tran* 1997. 1, 2925-2929.
19. Lyons, Bruce A. *J. Immunol. Methods* 2004. 243, 147-154.
20. Sandhya Xavier Ph.D., Shannon MacDonald M.D., Jennifer Roth B.S., Maresa Caunt B.S., Abebe Akalu Ph.D., Danielle Morais B.S., Michael T. Buckley M.S., Leonard Liebes Ph.D., Silvia C. Formenti M.D. and Peter C. Brooks Ph.D. *International Journal of Radiation Oncology\*Biology\*Physics*, 65, 517-527, 2006.
21. Erkkil, A.; Majander, I.; Pihko, P. M. *Chemical Reviews* 2007, 107, 5416-5470.

What is claimed is:

1. A stable, isolated compound comprising a substantially pure reaction product of a transimination nucleophilic catalyst and a carbonyl molecule which forms an imine group, wherein said carbonyl molecule is a small molecule immunomodulator that forms Schiff base adducts with biological amines of the immune system, or is an adjuvant that forms Schiff base adducts with biological amines of the immune system, wherein said small molecule immunomodulator is tucaresol, isotucaresol or a carbonyl-containing derivative of tucaresol or isotucaresol.

2. A stable isolated compound comprising a substantially pure reaction product of a transimination nucleophilic catalyst and a carbonyl molecule which forms an imine group according to the chemical formula QS-21-Api or QS21-Xyl:

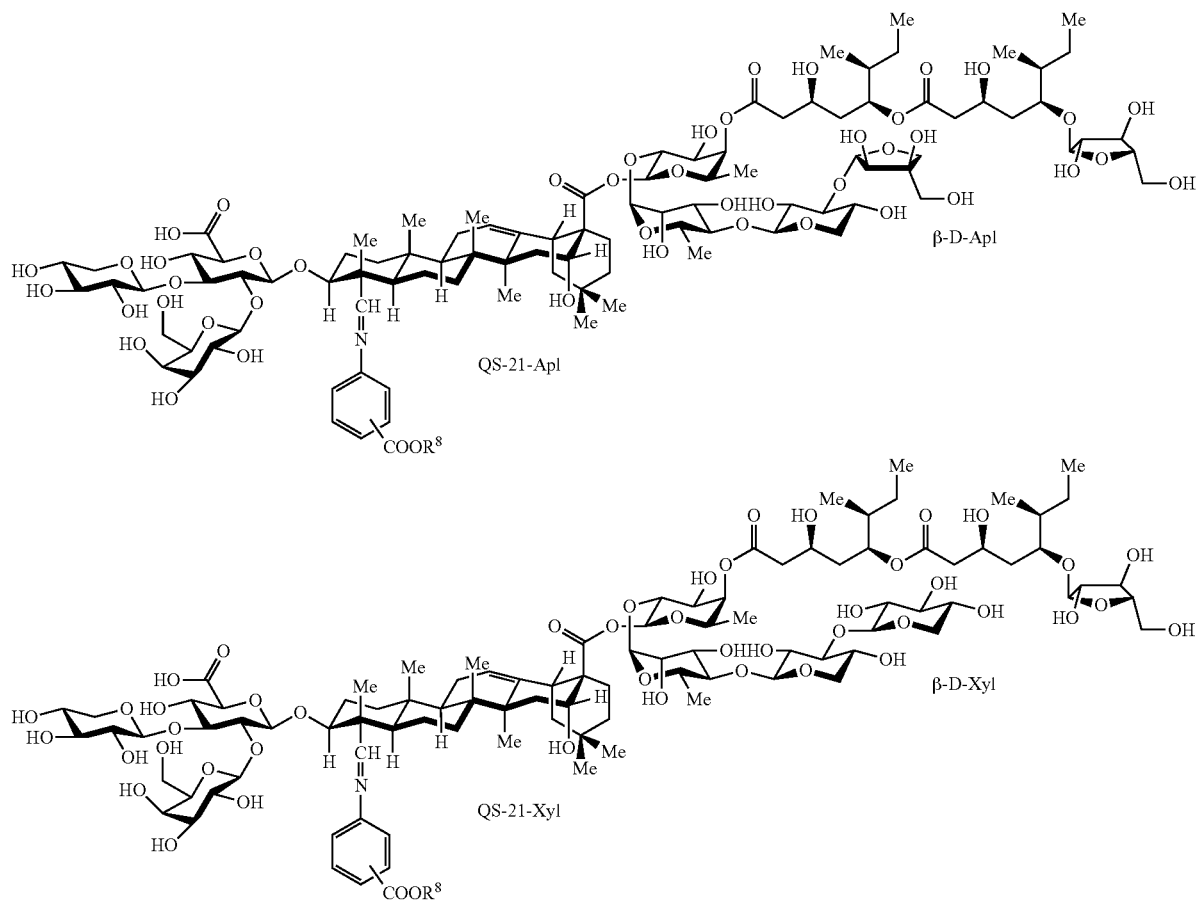

Where $R^8$ is H or an optionally substituted $C_1$-$C_{12}$ alkyl group, or a pharmaceutically acceptable salt thereof.

3. A compound according to the chemical formula:

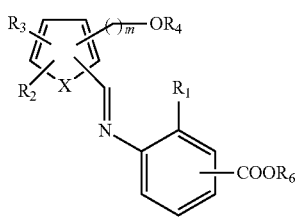

where

R1 is OH

R2 is H;

R3 is H or $CH_3$;

R4 is H or $CH_3$ or $CH_2CH_3$;

R6 is H or an unsubstituted $C_1$-$C_{12}$ alkyl; and

X=NH, $CHNH_2$O, S Se or P, or

A pharmaceutically acceptable salt or solvate thereof.

4. The compound according to claim 3 according to a chemical formula selected from the group consisting of

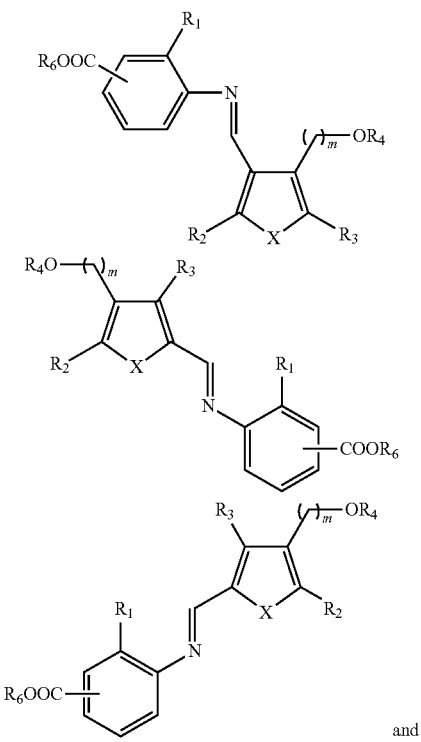

and

-continued

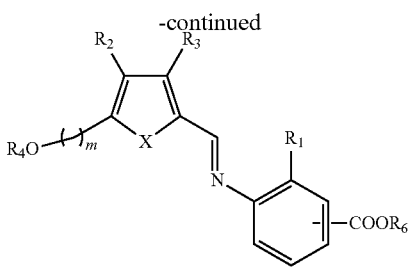

Or a pharmaceutically acceptable salt or solvate thereof.

5. A compound according to the chemical formula:

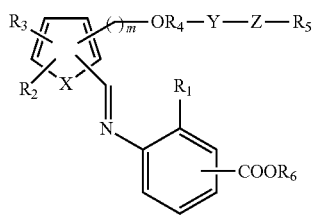

Where $R_1$ is an imine C=N—V, its tautomer, or a pharmacologically acceptable salt C=$^+$NH—V;

N—V is a transimination nucleophilic catalyst radical which is a 6-membered aromatic amine;

$R^2$ and $R^3$ are each independently H, OH, $C^1$-$C^{12}$ alkyl, $C^1$-$C^{12}$ alkoxy, $C^1$-$C^{12}$ hydroxyl-alkyl, halogen, aryl, or O-aryl;

$R^4$ and $R^5$ are each independently a substituted or unsubstituted aromatic or heteroaromatic moiety, a substituted or unsubstituted alkyl or alkylnoic acid or ester moiety;

M is an integer from 1 to 6;

X=NH, O, S, Se or P; and wherein Y is a chemical linker which includes one to four chemical moieties selected from the group consisting of CH2, CO, O, S, NH, NHCO and NHCONH;

Z is $(CH)_n$;

n is an integer from 1 to 4; and wherein Y and Z are interchangeable, or a pharmaceutically acceptable salt or solvate thereof.

6. The compound according to claim 5 wherein said N—V radical is obtained from p-aminobenzoic acid (PABA), OABA, MABA or a $C_1$-$C_{12}$ ester of PABA, OABA or MABA.

7. A compound according to claim 5 according to the chemical formula:

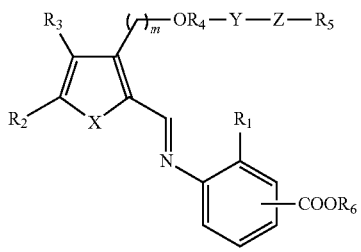

where $R_1$ is an H or OH;

$R_2$ is H;

$R_3$ is CH$_2$OH;

$R_4$ is an unsubstituted alkyl;

$R_5$ is an unsubstituted heteroaryl;

M is 1, 2, 3, 4, 5 or 6; and

X is O or S;

Y is a chemical linker which includes one to four chemical moieties selected from the group consisting of CH$_2$, CO, O, S, NH, NHCO and NHCONH;

Z is $(CH)_n$;

n is an integer from 1 to 4;

and Y and Z are interchangeable;

Or a pharmaceutically acceptable salt or solvate thereof.

8. The compound of claim 5 according to a chemical formula selected from group consisting of:

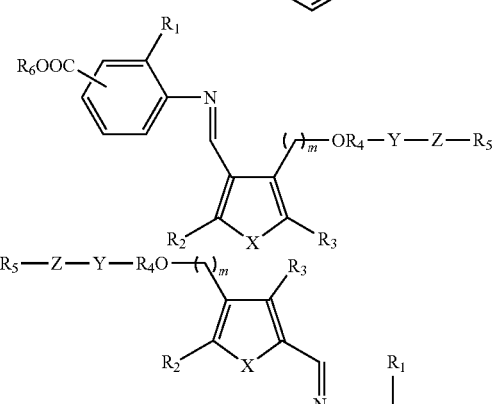

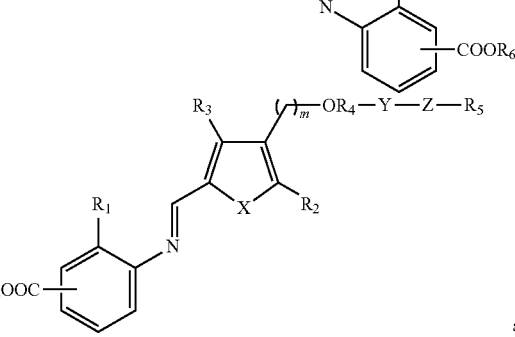

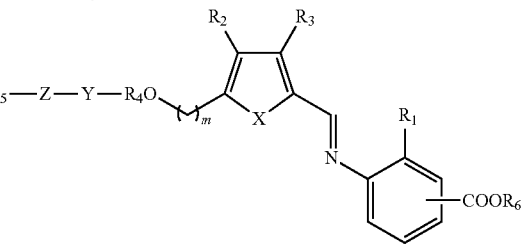

and

Or a pharmaceutically acceptable salt or solvate thereof.

9. A pharmaceutical composition comprising an effective amount of a compound according to claim 1 in combination with a pharmaceutically acceptable carrier additive or excipient.

10. A pharmaceutical composition comprising an effective amount of a compound according to claim 2 in combination with a pharmaceutically acceptable carrier additive or excipient.

11. A pharmaceutical composition comprising an effective amount of a compound according to claim 3 in combination with a pharmaceutically acceptable carrier additive or excipient.

12. A pharmaceutical composition comprising an effective amount of a compound according to claim 4 in combination with a pharmaceutically acceptable carrier additive or excipient.

13. A pharmaceutical composition comprising an effective amount of a compound according to claim 5 in combination with a pharmaceutically acceptable carrier additive or excipient.

14. A pharmaceutical composition comprising an effective amount of a compound according to claim 6 in combination with a pharmaceutically acceptable carrier additive or excipient.

15. A pharmaceutical composition comprising an effective amount of a compound according to claim 7 in combination with a pharmaceutically acceptable carrier additive or excipient.

16. A pharmaceutical composition comprising an effective amount of a compound according to claim 8 in combination with a pharmaceutically acceptable carrier additive or excipient.

* * * * *